United States Patent
Matsumoto et al.

(10) Patent No.: US 8,912,298 B2
(45) Date of Patent: Dec. 16, 2014

(54) METHOD FOR PRODUCING PARTICULATE WATER ABSORBING AGENT CONTAINING WATER ABSORBENT RESIN AS MAIN COMPONENT

(75) Inventors: Koji Matsumoto, Hyogo (JP); Shuji Kanzaki, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 200 days.

(21) Appl. No.: 12/934,381

(22) PCT Filed: Mar. 31, 2009

(86) PCT No.: PCT/JP2009/056659
§ 371 (c)(1),
(2), (4) Date: Sep. 24, 2010

(87) PCT Pub. No.: WO2009/123193
PCT Pub. Date: Oct. 8, 2009

(65) Prior Publication Data
US 2011/0039961 A1 Feb. 17, 2011

(30) Foreign Application Priority Data

Mar. 31, 2008 (JP) .................. 2008-089389
Mar. 31, 2008 (JP) .................. 2008-089425

(51) Int. Cl.
*C08J 9/28* (2006.01)
(Continued)

(52) U.S. Cl.
CPC .............. *C08J 3/245* (2013.01); *C08F 220/06* (2013.01); *C08F 2/48* (2013.01);
(Continued)

(58) Field of Classification Search
USPC .......... 366/136, 137, 152.1; 521/64; 526/240
See application file for complete search history.

(56) References Cited

U.S. PATENT DOCUMENTS 4,985,518 A * 1/1991 Alexander et al. ............ 526/240
5,322,896 A 6/1994 Ueda et al.
(Continued)

FOREIGN PATENT DOCUMENTS

DE 19543368 5/1997
EP 0873185 10/1998
(Continued)

OTHER PUBLICATIONS

Klein, J.A.; Mros, G.R. "Characterization and Safe Handling of Reactive Initiator Solutions" Published online Oct. 13, 2006. Wiley Interscience. Process Safety Progress, vol. 25, No. 4. pp. 303-310.*

(Continued)

*Primary Examiner* — Randy Gulakowski
*Assistant Examiner* — Christina Wales
(74) *Attorney, Agent, or Firm* — Roylance, Abrams, Berdo & Goodman, L.L.P.

(57) ABSTRACT

An apparatus (2) includes: a first tank (4); a line mixer (6); a second tank (8); a cooling jacket (10); a first tube (12); a second tube (14); and a third tube (16). In the first tank (4), (i) sodium persulfate serving as a polymerization initiator and (ii) water are fed so as to obtained an aqueous solution. The aqueous solution is continuously taken out and transferred via the first tube (12) to the line mixer (6). Between the first tank (4) and the line mixer (6), water is injected into the first tube (12). The water and the sodium persulfate aqueous solution are stirred together in the line mixer (6). This stirring decreases a concentration of the aqueous solution. The resulting aqueous solution is continuously fed to the second tank (8) via the second tube (14). The aqueous solution is then continuously taken out via the third tube (16) and is continuously added to an acrylic acid (salt) aqueous solution. This provides a production method which allows a high-quality water absorbing agent to be obtained with a compact apparatus.

14 Claims, 5 Drawing Sheets

(51) Int. Cl.
| | |
|---|---|
| *C08F 220/06* | (2006.01) |
| *C08F 2/48* | (2006.01) |
| *C08F 2/10* | (2006.01) |
| *C07C 51/50* | (2006.01) |
| *C07C 51/41* | (2006.01) |
| *C08F 20/06* | (2006.01) |
| *C08J 3/24* | (2006.01) |
| *A61L 15/60* | (2006.01) |
| *B01J 19/00* | (2006.01) |
| *C08F 222/10* | (2006.01) |

(52) U.S. Cl.
CPC . *C08F 2/10* (2013.01); *C07C 51/50* (2013.01); *C07C 51/41* (2013.01); *C08F 20/06* (2013.01); *C08J 2333/02* (2013.01); *A61L 15/60* (2013.01); *C08F 222/1006* (2013.01); *B01J 2219/00006* (2013.01); *B01J 19/0086* (2013.01)
USPC ............ 526/240; 137/255; 137/256; 137/571

(56) References Cited

U.S. PATENT DOCUMENTS

| | | | |
|---|---|---|---|
| 5,522,660 A * | 6/1996 | O'Dougherty et al. ....... 366/136 |
| 6,143,821 A | 11/2000 | Houben | |
| 6,716,894 B2 | 4/2004 | Kajikawa et al. | |
| 6,727,345 B2 * | 4/2004 | Kajikawa et al. ......... 528/502 R |
| 6,817,557 B2 | 11/2004 | Kakita et al. | |
| 7,193,006 B2 | 3/2007 | Ishizaki et al. | |
| 7,265,190 B2 | 9/2007 | Dairoku et al. | |
| 2003/0020199 A1 | 1/2003 | Kajikawa et al. | |
| 2004/0092688 A1 | 5/2004 | Dairoku et al. | |
| 2007/0238806 A1 | 10/2007 | Mitsukami et al. | |
| 2008/0194863 A1 | 8/2008 | Weismantel et al. | |
| 2008/0227932 A1 | 9/2008 | Funk et al. | |
| 2008/0242816 A1 | 10/2008 | Weismantel et al. | |
| 2009/0036855 A1 * | 2/2009 | Wada et al. ................... 604/372 |
| 2009/0221746 A1 | 9/2009 | de Marco et al. | |
| 2009/0318885 A1 * | 12/2009 | Dairoku et al. ............... 604/367 |
| 2011/0003926 A1 * | 1/2011 | Nogi et al. ................... 524/401 |

FOREIGN PATENT DOCUMENTS

| | | |
|---|---|---|
| EP | 1191051 | 3/2002 |
| EP | 1840137 | 10/2007 |
| JP | 6-200046 | 7/1994 |
| JP | 11240903 | 9/1999 |
| JP | 200382107 | 3/2003 |
| JP | 2004155963 | 6/2004 |
| JP | 2006-160846 A * | 6/2006 |
| JP | 2006160846 | 6/2006 |
| WO | 2007023097 | 3/2007 |
| WO | 2007028746 | 3/2007 |
| WO | 2007028747 | 3/2007 |
| WO | 2007028751 | 3/2007 |

OTHER PUBLICATIONS

"Perry's Chemical Engineers' Handbook (7th Ed.)" Published by McGraw-Hill, copyright 1997, released online Mar. 1, 2001. Edited by Perry, R.H.; Green, D.W. Section 18: Liquid-Solid Operations and Equipment. pp. 18-1, 2, 5-8, 13-15, 18-21.*
Johnson, B.S. Course 10.450 Process Dynamics, Operations, and Control, Spring 2006. Lesson 3: The Blending Tank Revised Jan. 13, 2005. (Massachusetts Institute of Technology: MIT OpenCourseWare), http://ocw.mit.edu (accessed Jun. 20, 2012). License: Creative Commons BY-NC-SA. pp. 1-22.*
Faanes, A.; Skogestad, S. "Buffer Tank Design for Acceptable Control Performance" Published on the Web: Apr. 8, 2003. Ind. Eng. Chem. Res. 2003, 42, pp. 2198-2208.*
"Modern Superabsorbent Technology" ed. by Buchholz, F. L; Graham, A.T. Published by Wiley-VCH, copyright 1998. pp. 69, 77-83.*
Faanes, A.; Skogestad, S. "Buffer Tank Design for Acceptable Control Performance" Ind. Eng. Chem. Res. 2003, 42, pp. 2198-2208.*
Johnston, Barry S. 10.450 Process Dynamics, Operations, and Control,Spring 2006. (Massachusetts Institute of Technology)"Process Dynamics, Operations and Control Lesson 3: the blending tank" revised Jan. 13, 2005. Available online at http://ocw.mit.edu. License: Creative Commons BY-NC-SA.*
Klein, J.A.; Mros, G.R. "Characterization and Safe Handling of Reactive Initiator Solutions" Process Safety Progress vol. 25, No. 4, pp. 303-310. Published online Oct. 13, 2006.*
Graham, A.T.; Wilson, L.R. "Commercial Processes for the Manufacture of Superabsorbent Polymers" in Modern Superabsorbent Polymer Technology ed by F.L. Buchholz and A.T. Graham. 1998. pp. 69, 77-84.*
Masucci, S. "Why in-line mixing?" available online at http://www.bematek.com/files/In-Line%20Mixing.pdf copyright 2005.*
Buchholz, F.L. "Preparation Methods of Superabsorbent Polyacrylates" Chp. 2 of "Superabsorbent Polymers" ed. by F. Buchholz. 1994. ACS symposium series. pp. 27-38.*
Supplementary European Search Report dated Nov. 19, 2012, from the European Patent Office in corresponding European Application No. 09726747.0.

* cited by examiner

METHOD FOR PRODUCING PARTICULATE WATER ABSORBING AGENT CONTAINING WATER ABSORBENT RESIN AS MAIN COMPONENT

TECHNICAL FIELD

The present invention relates to a method for producing a particulate water absorbing agent containing a water absorbent resin as a main component.

BACKGROUND ART

A particulate water absorbing agent containing a water absorbent resin as a main component is used in sanitary materials such as a disposable diaper, a sanitary napkin, and an incontinence pad. The water absorbent resin absorbs body fluids such as urine and blood. Known examples of the water absorbent resin encompass: a partially neutralized cross-linked polymer of polyacrylic acid; a hydrolyzed starch-acrylic acid graft polymer; a saponified vinyl acetate-acrylic ester copolymer; a hydrolyzed or cross-linked acrylonitrile copolymer; a hydrolyzed or cross-linked acrylamide copolymer; and a cross-linked cationic monomer. Among these, a partially neutralized cross-linked polymer of polyacrylic acid is particularly preferable in terms of performance and cost.

A polyacrylic acid (salt) water absorbent resin, particularly a particulate water absorbing agent containing a partially neutralized polymer of polyacrylic acid, is produced by the following method: First, a monomer containing acrylic acid salt is polymerized with use of a polymerization initiator so as to obtain a hydrogel. This hydrogel is dried and pulverized so as to obtain water absorbent resin particles. The water absorbent resin particles are then surface-cross-linked according to need with use of a surface cross-linking agent. Further, a surface reforming additive is added to surfaces of the respective water absorbent resin particles according to need so as to finally obtain a particulate water absorbing agent.

In order to obtain a high-quality particulate water absorbing agent, it has conventionally been necessary, for example, to sufficiently mix a monomer aqueous solution and the polymerization initiator during the polymerizing step. This requires the polymerization initiator to be in a form of a low-concentration aqueous solution. As a result, a large amount of such an aqueous solution is necessary, and also a tank for storing the aqueous solution needs to have a large capacity.

In a case where an operation of a production plant is suspended for a reason such as trouble in or maintenance of the production plant, a supply of the aqueous solution and the like for the polymerization initiator is also suspended. In this case, the aqueous solution is kept stored in a tank for an extended period of time. While the aqueous solution is stored in the tank, a chemical reaction may occur in the aqueous solution and unfortunately impair a function of the polymerization initiator. In view of the fact that such an aqueous solution having an impaired function is discarded, if the tank has a large capacity, an amount of the aqueous solution to be discarded is large accordingly. This not only is uneconomical, but also requires a long time and high cost for waste liquid disposal.

Another example method for producing a particulate water absorbing agent containing a water absorbent resin as a main component is a method of mixing an additive and the like by line mixing. This method, however, produces solutions which differ from one another in concentration and which are thus unstable in concentration. It follows that particulate water absorbing agents obtained in accordance with the method differ from one another in quality and are thus unstable in quality.

In relation to the above problems, the following techniques have been known conventionally: European Patent No. 0,873,185 discloses a particulate polymer obtained from a reaction between (i) a monomer and (ii) a polymerization initiator stored in a tank in which a temperature is controlled at a predetermined temperature.

U.S. Pat. No. 7,265,190 discloses a method for producing a water absorbent resin in which method a polymerization initiator is added to a monomer liquid while the monomer liquid is in a tube for transporting it. This production method allows property values of a water absorbent resin to be stable by removing a water absorbent resin which has a property value that falls outside a predetermined range. This method, however, requires mixing such a removed water absorbent resin again and thus requires a complicated process.

U.S. Pat. No. 4,985,518 discloses a method for producing a water absorbent resin in which method a polymerization initiator and monomer liquid stored in respective tanks are mixed in a line mixer and then fed to a belt polymerization device. This production method uses polymerization heat to simultaneously carry out polymerization and drying so as to obtain a solid water absorbent resin. The water absorbent resin thus obtained, however, has a low water absorbing property.

PCT international publications 2007/028746 pamphlet, 2007/028747 pamphlet, and 2007/028751 pamphlet each disclose a method for producing a water absorbent resin which method includes a continuous neutralization step in which an acrylic acid and a base are mixed with each other. In these methods, a liquid containing materials (i.e., a monomer and a polymerization initiator) of a water absorbent resin is stored in a tank.

PCT international publication 2007/023097 pamphlet discloses a method for producing a water absorbent resin which method includes two systems for a polymerizing step of a water absorbent resin but has a single system for a production process after the polymerizing step. With this production method, a water absorbent resin obtained has stable property values. This production method, however, requires a plurality of polymerization devices and thus requires a complicated process.

Methods similar to the above are also disclosed in U.S. Pat. Nos. 6,716,894, 6,817,557, 7,193,006, 6,727,345, and PCT international publication 2007/023097 pamphlet.

CITATION LIST

Patent Literature 1
European Patent No. 0,873,185
Patent Literature 2
U.S. Pat. No. 7,265,190
Patent Literature 3
U.S. Pat. No. 4,985,518
Patent Literature 4
PCT international publication 2007/028746 pamphlet
Patent Literature 5
PCT international publication 2007/028747 pamphlet
Patent Literature 6
PCT international publication 2007/028751 pamphlet
Patent Literature 7
U.S. Pat. No. 6,716,894
Patent Literature 8
U.S. Pat. No. 6,817,557

Patent Literature 9
U.S. Pat. No. 7,193,006
Patent Literature 10
U.S. Pat. No. 6,727,345
Patent Literature 11
PCT international publication 2007/023097 pamphlet

SUMMARY OF INVENTION

Technical Problem

A particulate water absorbing agent containing a water absorbent resin as a main component has various property values (e.g., centrifuge retention capacity, absorbency against pressure, water absorption rate, liquid permeability, and gel stability) which need to be controlled in accordance with an application. However, in a case where the particulate water absorbing agent is produced continuously in large quantities, it is difficult to stabilize the property values. Even a slight difference in property values of the particulate water absorbing agent may impair quality of a finished product such as a disposable diaper and a sanitary napkin. Further, since many properties are simultaneously controlled, there occurs a decrease in productivity and a disposal loss due to failure to meet specifications. Under the circumstances, there is a problem that even in a case where the above production methods disclosed in the respective literatures are employed in a plant which mass-produces a particulate water absorbing agent, a particulate water absorbing agent obtained still has unstable properties.

In view of the above problem, it is an object of the present invention to provide a method for producing a particulate water absorbing agent containing a water absorbent resin as a main component which method does not require a large-capacity tank and which allows production of a particulate water absorbing agent which is excellent in quality stability.

Solution to Problem

The inventors of the present invention have diligently conducted research on stability of properties of a particulate water absorbing agent in its continuous production, and thus completed the present invention. Specifically, the inventors first focused on a liquid containing a polymerization initiator and a liquid containing a modifier, which liquids are not focused on in literatures such as Patent Literatures 1 to 11 above. The inventors consequently found that a variation in quality of the particulate water absorbing agent is caused by a merely slight variation or change (e.g., concentration decrease due to decomposition) in concentration of the liquid containing a polymerization initiator and the liquid containing a modifier even if steps such as a polymerizing step and a mixing step are under strict control. Further, the inventors found that it is possible to stabilize and improve the properties of a target particulate water absorbing agent by providing a particular step for adjusting the modifier, and thus completed the present invention.

A method of the present invention for producing a particulate water absorbing agent containing a water absorbent resin as a main component includes the steps of: (1) mixing, with an aqueous solution of a monomer for a water absorbent resin, a liquid containing a polymerization initiator; (2) polymerizing the monomer so as to obtain a hydrogel (hereinafter referred to also as "hydrogel polymer"); (3) drying the hydrogel so as to obtain a dried polymer; and (4) adding, to either the aqueous solution of the monomer or the polymer, a liquid containing a modifier, either the liquid containing the polymerization initiator or the liquid containing the modifier being obtained through the steps of: (a) providing at least two kinds of liquids; and (b) continuously feeding the at least two kinds of liquids to a tank either separately or together while continuously taking out a mixture solution of the at least two kinds of liquids from the tank. According to this production method, the step (4), in which a liquid containing a modifier is added to either the aqueous solution of the monomer or the polymer, is not essential. Further, the steps (a) and (b) are preferably carried out a plurality of times.

The polymer, to which the modifier is added, stands for either the hydrogel polymer obtained by the polymerization or its dried polymer. The polymer is, however, preferably the dried polymer. Thus, the modifier (preferably a surface cross-linking agent) is added to dried water absorbent resin particles.

In the step (b), the mixture solution in the tank may preferably be circulated via a circulation loop. The mixture solution may be cooled or heated in the circulation loop. The mixture solution may be cooled or heated in the tank. One of the at least two kinds of liquids provided in the step (a) may preferably be an aqueous solution.

In the step (a), (i) an aqueous solution of the polymerization initiator comprising at least one kind of polymerization initiator and (ii) water may preferably be provided. It may be preferable that the aqueous solution, provided in the step (a), of the polymerization initiator has a concentration of not less than 20 mass % but not more than 50 mass %; and the aqueous solution of the polymerization initiator has a concentration of not less than 1 mass % but not more than 25 mass % after the aqueous solution is diluted through the step (b). The polymerization initiator may preferably be contained in an amount of not less than 0.001 part by mass but not more than 2 parts by mass with respect to 1 mole of the monomer.

In the step (a), (i) a liquid including at least one kind of surface cross-linking agent serving as the modifier and (ii) water may preferably be provided. The at least one kind of surface cross-linking agent may preferably be contained in an amount of not less than 0.001 part by mass but not more than 10 parts by mass with respect to 100 parts by mass of a solid content of the polymer.

In the step (a), (i) an aqueous solution of the modifier for a surface-cross-linked polymer and (ii) a liquid including an auxiliary dispersing agent may preferably be provided. The modifier may preferably be contained in an amount of not less than 0.0001 part by mass but not more than 10 parts by mass with respect to 100 parts by mass of a solid content of the polymer.

It may be preferable that in the step (a), the modifier comprises a surface cross-linking agent, and the additive is used after surface cross-linking performed by the surface cross-linking agent.

The modifier may preferably include one selected from the group consisting of a surface cross-linking agent, a surface active agent, a chelating agent, a deodorant agent, an antibacterial agent, a reducing agent, and an anti-coloring agent.

Another method of the present invention for producing a water absorbing agent containing a water absorbent resin as a main component includes the steps of: (1) mixing, with an aqueous solution of a monomer for a water absorbent resin, a liquid containing a polymerization initiator; (2) polymerizing the monomer so as to obtain a hydrogel (hereinafter referred to also as "hydrogel polymer"); and (3) drying the hydrogel so as to obtain a dried polymer, the liquid containing the polymerization initiator being obtained through the steps of: (a) providing at least two kinds of liquids; and (b) continuously feeding the at least two kinds of liquids to a tank either separately or together while continuously taking out a mixture solution of the at least two kinds of liquids from the tank.

It may be preferable that: in the step (b), a flow rate is controlled to satisfy $0.95 \leq x/y \geq 1.05$, where x is an amount of the at least two kinds of liquids fed to the tank and y is an amount of the at least two kinds of liquids taken out from the tank; and the at least two kinds of liquids is stored in the tank in an amount which is controlled so that the amount is not less than 10% but not more than 90% of a capacity of the tank.

It may be preferable that: the water absorbent resin comprises a polyacrylic acid water absorbent resin and/or a polyacrylic acid salt water absorbent resin (hereinafter, polyacrylic acid and/or polyacrylic acid salt is expressed as polyacrylic acid (salt) as appropriate); and the polymerization is a continuous kneader polymerization or a continuous belt polymerization.

The water absorbing agent may preferably be continuously produced at not less than 1000 kg/hr per one line or per one plant.

At least one dehydration esterification surface cross-linking agent selected from the group consisting of an oxazolidinone compound, an alkylenecarbonate compound, a polyhydric alcohol compound, and an oxetane compound may preferably be added to the dried polymer as the modifier.

A plurality of covalent bonding or ionic bonding surface cross-linking agents may preferably be added as the modifier to the dried polymer either simultaneously or separately.

The polymerization initiator may preferably be a water-soluble pyrolytic polymerization initiator which is used in combination with a reducing agent.

It may be preferable that: the particulate water absorbing agent contains a polyacrylic acid (salt) water absorbent resin as the main component; and (i) an absorbency against pressure (AAP) of the particulate water absorbing agent for physiological saline under a pressure of 4.8 kPa falls within a range from 15 g/g to 35 g/g, and/or (ii) a liquid permeability (SFC) of the particulate water absorbing agent is not less than 30 ($\times 10^{-7} \cdot cm^3 \cdot s \cdot g^{-1}$).

Additional objects, features, and strengths of the present invention will be made clear by the description below. Further, the advantages of the present invention will be evident from the following explanation in reference to the drawings.

BRIEF DESCRIPTION OF DRAWINGS

FIG. 1 is a conceptual diagram illustrating a series of devices for use in a production method of the present invention.

FIG. 2 is a conceptual diagram illustrating another series of devices for use in a production method of the present invention.

FIG. 3 is a conceptual diagram illustrating still another series of devices for use in a production method of the present invention.

FIG. 4 is a conceptual diagram schematically illustrating (i) a storage tank, provided with a jacket type cooling/heating device, which can be used in an embodiment of the present invention and (ii) a vicinity of the storage tank.

FIG. 5 is a conceptual diagram schematically illustrating (i) a storage tank, provided with a coil type cooling/heating device, which can be used in the embodiment of the present invention and (ii) a vicinity of the storage tank.

FIG. 6 is a conceptual diagram schematically illustrating (i) a storage tank, externally provided with a shell-and-tube type heat exchanger, which can be used in the embodiment of the present invention and (ii) a vicinity of the storage tank.

Figure 1:
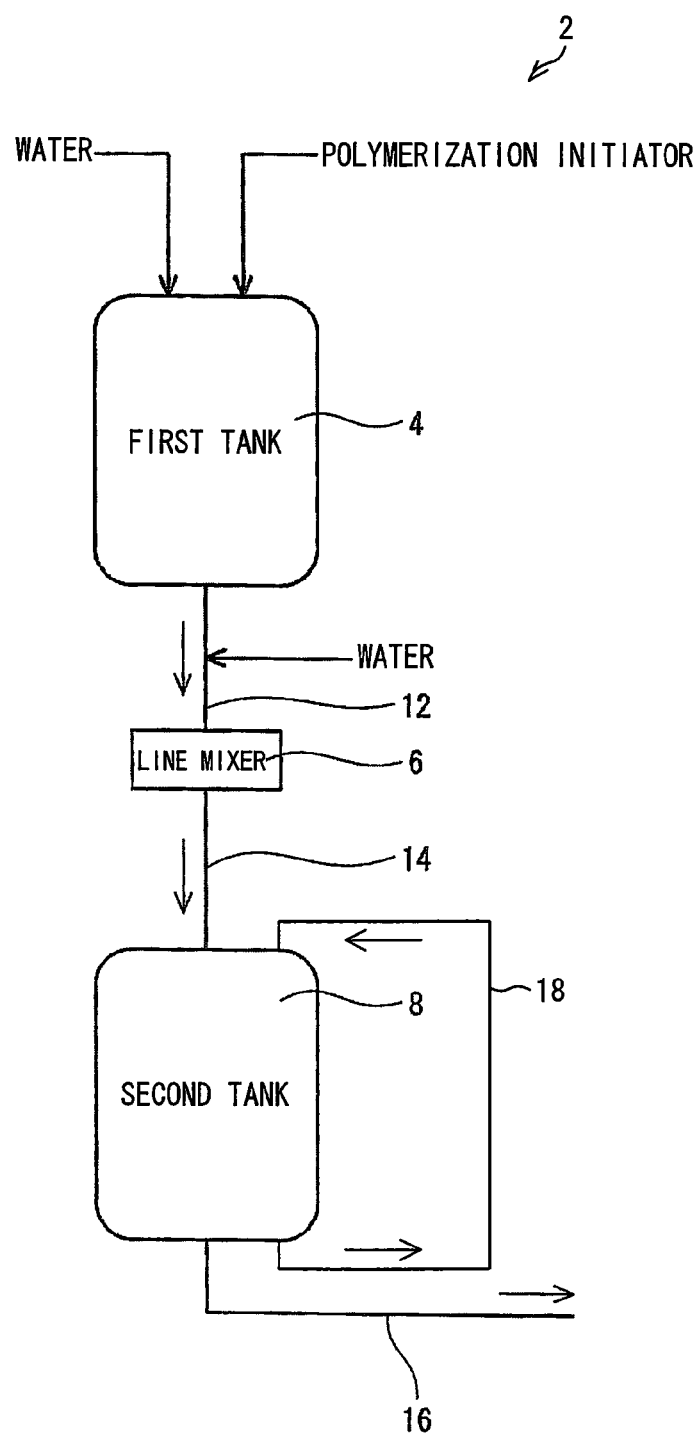
FIG. 1

REFERENCE SIGNS LIST 2, 20, 44 apparatus
4, 22, 46 first tank
6, 28, 52 line mixer
8, 24, 48 second tank
26, 50 third tank
30, 54 fourth tank
12, 32, 58 first tube
14, 34, 60 second tube
16, 36, 62 third tube
18, 38, 64 fourth tube
40, 66 fifth tube
42, 68 sixth tube
100 jacket
101 coil
102 heat exchanger

DESCRIPTION OF EMBODIMENTS

The following description deals in detail with a method of the present invention for producing a particulate water absorbing agent containing a water absorbent resin as a main component. The scope of the present invention is, however, not limited to the description below. The present invention can thus be altered as appropriate for implementation other than examples below without departing from the spirit of the present invention.

(1) Definitions of Terms
(a) "Water Absorbent Resin"

The term "water absorbent resin" used in the present specification stands for a water-swelling and water-insoluble polymer gelatinizer which has (i) an absorption capacity (CRC; defined in a description of the Examples) of not less than 5 g/g, preferably within a range from 10 to 100 g/g, and more preferably within a range from 20 to 80 g/g, and (ii) a water-soluble content (extractables; defined in accordance with ERT 470.2-02 (2002)) within a range from 0 to 50 mass %, preferably within a range from 0 to 30 mass %, more preferably within a range from 0 to 20 mass %, and particularly preferably within a range from 0 to 10 mass %. Note that the water absorbent resin is not limitedly 100% polymer. The water absorbent resin can thus include, for example, later-described additives to an extent to which the above properties are maintained.

(b) "Polyacrylic Acid (Salt)"

The term "polyacrylic acid (salt)" (polyacrylic acid and/or polyacrylic acid salt) used in the present specification stands for a polymer containing a repeating unit of acrylic acid (salt) as a main component. Specifically, the term stands for a polymer including, as a monomer other than a cross-linking agent, acrylic acid (salt) within a range from 50 to 100 mol %, preferably within a range from 70 to 100 mol %, more preferably within a range from 90 to 100 mol %, and particularly preferably at substantially 100 mol %. The salt as the polymer encompasses a water-soluble salt, and is preferably a monovalent salt and more preferably an alkali metal salt or an ammonium salt. Among these salts, an alkali metal salt is preferable, and sodium salt is particularly preferable.

(c) "Water Absorbing Agent"

The term "water absorbing agent" used in the present specification stands for a gelatinizer of an aqueous liquid which gelatinizer contains a water absorbent resin as a main component. The aqueous liquid is not limited to water, but may include urine, blood, feces, waste fluid, moisture, vapor, ice, a mixture of water and an organic solvent and/or inorganic solvent, rain water, groundwater, etc. The aqueous liquid is not particularly limited to a specific one, provided that it contains water. Among the above, the aqueous liquid is preferably urine, particularly human urine. The water absorbent resin (polyacrylic acid (salt) water absorbent resin) of the present invention is preferably contained in an amount which falls within a range from 70 to 99.9 weight %, more preferably within a range from 80 to 99.7 weight %, and even more preferably within a range from 90 to 99.5 weight %, with respect to a total weight of the water absorbing agent. In view of a water absorption rate and an impact resistance of the particulate water absorbing agent (particles), the water absorbing agent can contain a component other than the water absorbent resin, which component is preferably water. The water absorbing agent can also contain later-described additives according to need.

(d) "EDANA" and "ERT"

"EDANA" is an acronym for the European Disposables and Nonwovens Association. "ERT" is an acronym for the EDANA Recommended Test Methods, which are European standard (and almost world standard) methods for measuring properties of a water absorbent resin. In the present specification, properties of a water absorbent resin are measured in reference to the ERT original text (known literature; revised in 2002) unless otherwise stated.

(e) Particles

The term "particles" used in the present specification stands for a solid which has fluidity and a particle diameter of not more than 5 mm in accordance with sieve classification. A water content of the particles is not particularly limited to a specific one, provided that the particles are a solid. The water content is normally less than 30 weight %, and more preferably not more than 20 weight %. The particle diameter has a lower limit of, e.g., 1 nm. Further, the solid is simply required to be in a form of powder having a certain fluidity. The solid, for example, has a measurable flow rate (in accordance with ERT 450.2-02 (2002)) or can be subjected to sieve classification (in accordance with ERT 420.2-02 (2002)). The solid is not particularly limited in shape, and can thus have an irregularly-pulverized shape, a spherical shape, or a substantially spherical shape, or have a form of granulated particles (agglomerates) of any of the above. The solid preferably includes particles having an irregularly-pulverized shape.

Further, in the present specification, a range "from X to Y" stands for "not less than X but not more than Y." In addition, the term "ton (t)", which is a unit of weight, stands for "metric ton."

(2) Method for Producing Particulate Water Absorbing Agent

A production process of the present invention for producing a particulate water absorbing agent includes a polymerizing step, a drying step, a pulverizing step, a classifying step, a surface cross-linking step, a cooling step, an additive adding step, a granulating step, and a filling step. The following description deals with these steps in detail.

[Polymerizing Step]

In the polymerizing step of the present invention, a monomer for the water absorbent resin is subjected to a polymerization reaction so as to obtain a hydrogel. A method for the polymerization is not particularly limited to a specific one. Examples of the method encompass aqueous solution polymerization, reverse phase suspension polymerization, bulk polymerization, precipitation polymerization, etc. Among these, because the polymerization reaction is easy to control and a high-quality particulate water absorbing agent can be obtained, aqueous solution polymerization and reverse phase suspension polymerization are preferable, aqueous solution polymerization is more preferable, and continuous aqueous solution polymerization is particularly preferable. Continuous aqueous solution polymerization can be carried out by, e.g., (i) a method in which a hydrogel obtained in a kneader such as a one-shaft or multiple-shaft kneader (preferably a double-arm kneader) is simultaneously pulverized and polymerized (hereinafter referred to as "continuous kneader polymerization") or (ii) a method in which a monomer aqueous solution is fed into a predetermined container or onto a driven belt so that a polymerization is carried out (hereinafter referred to as "continuous belt polymerization").

The monomer for the water absorbent resin to be included in the particulate water absorbing agent according to the present embodiment of the invention is not particularly limited to a specific one. Examples of the monomer encompass: (i) monomers containing an acid group and a salt thereof, the monomers including, e.g., (meth)acrylic acid, maleic acid (anhydride), itaconic acid, cinnamic acid, vinyl sulfonic acid, allyltoluene sulfonic acid, vinyl toluene sulfonic acid, styrene sulfonic acid, 2-(meth)acrylamide-2-methylpropanesulfonic acid, 2-(meth)acryloyl ethane sulfonic acid, 2-(meth)acryloyl propane sulfonic acid, etc.; (ii) an unsaturated monomer containing a mercapto group; (iii) an unsaturated monomer containing a phenolic hydroxyl group; (iv) an unsaturated monomer containing an amide group, such as (meth)acrylamide, N-ethyl(meth)acrylamide, N,N-dimethyl(meth)acrylamide, etc.; and (v) an unsaturated monomer containing an amino group, such as N,N-dimethylamino ethyl(meth)acrylate, N,N-dimethyl aminopropyl(meth)acrylate, N,N-dimethyl aminopropyl(meth)acrylamide, etc. These monomers can be used independently, or two or more of them can be mixed for use as appropriate.

In view of a property and cost of a particulate water absorbing agent to be obtained, the water absorbent resin is preferably based on polyacrylic acid (salt). The water absorbent resin thus preferably contains as a main component an acrylic acid and/or its salt (e.g., a salt of sodium, lithium, potassium, ammonium, or an amine; among these, sodium salt is preferable in terms of cost). The acrylic acid and/or its salt is/are preferably contained in an amount which is not less than 50 mol %, more preferably not less than 80 mol %, and particularly preferably 95 mol % (upper limit: 100 mol %), with respect to a total amount of the monomer (other than a cross-linking agent).

In a case where the monomer containing an acid group is used, the monomer is preferably totally or partially neutralized. The monomer of the present invention encompasses both "unneutralized monomer" and "salt produced by neutralization". The use of the salt allows an improvement in efficiency of a polymerization reaction and a reduction in amount of an unreacted monomer (residual monomer) contained in the particulate water absorbing agent.

In the case where the monomer is a monomer containing an acid group, a neutralization ratio of the monomer is not particularly limited to a specific one. The neutralization can be carried out according to need with respect to a polymer gel after the polymerization. The neutralization carried out after the polymerization is unnecessary for an application as a product, such as a sanitary material, which may be in contact with a human body. The neutralization ratio preferably falls within a range from 30 to 100 mol %, more preferably within a range from 40 to 95 mol %, and even more preferably within a range from 50 to 90 mol %, with respect to the polymer. It is possible to reduce amounts of the residual monomer and residual basic substance contained in the particulate water absorbing agent, by setting the neutralization ratio within one of the above ranges. As a result, it is possible to improve safety and economic efficiency.

In a case where the monomer is used in a form of an aqueous solution during the polymerizing step, a monomer concentration of the aqueous solution (hereinafter referred to as "monomer aqueous solution") is not particularly limited to a specific one. The monomer concentration preferably falls within a range from 20 to 65 mass %, more preferably within a range from 30 to 65 mass %, and particularly preferably within a range from 40 to 60 mass %. It is possible to achieve a high productivity and obtain a high-quality particulate water absorbing agent by setting the monomer concentration within one of the above ranges. It follows that it is possible to obtain a hydrogel polymer having a solid content concentration which is less than 80 mass % or which even falls within a range from 20 to 70 mass %, by polymerizing the monomer aqueous solution having a monomer concentration within one of the above ranges.

During the polymerizing step, an internal cross-linking agent can be added to the monomer aqueous solution according to need. By thus adding the internal cross-linking agent, it is possible to reduce dissolution of the particulate water absorbing agent when the particulate water absorbing agent absorbs, for example, a body fluid such as urine, blood, etc. The internal cross-linking agent is not particularly limited to a specific one. An example of the internal cross-linking agent is a compound having in a single molecule two or more polymerizable unsaturated groups or reactive groups. In particular, a compound having in a single molecule two or more polymerizable unsaturated groups is preferable. Specific examples of such a compound encompass N,N'-methylene bis(meth)acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethylene oxide denatured trimethylolpropane tri(meth)acrylate, pentaerythritol hexa(meth)acrylate, triallyl cyanurate, triallyl isocyanurate, triallyl phosphate, triallyl amine, polyallyloxyalkane, (poly)ethyleneglycol diglycidyl ether, glycerol diglycidyl ether, ethylene glycol, polyethyleneglycol, propylene glycol, glycerin, 1,4-butandiol, pentaerythritol, ethylenediamine, ethylene carbonate, propylene carbonate, polyethylene imine, glycidyl(meth)acrylate, etc. In view of reactivity, the above internal cross-linking agents can be used solely, or alternatively, two or more of them can be used in combination.

The internal cross-linking agent can be contained in an amount which is determined as appropriate depending on desired properties of the particulate water absorbing agent. The amount normally preferably falls within a range from 0.001 to 5 mol %, and more preferably within a range from 0.01 to 5 mol %, with respect to the monomer component. A water-soluble content of the particulate water absorbing agent is reduced by containing the internal cross-linking agent in an amount which is not less than 0.001 mol %. Further, it is possible to obtain a particulate water absorbing agent having an excellent absorption capacity, by containing the internal cross-linking agent in an amount which is not more than 5 mol %.

Further, during the polymerizing step, a foaming agent, a hydrophilic polymer, a surface active agent, a chain transfer agent and/or the like can be added according to need to the monomer aqueous solution or to a gel which is in process of polymerization. Examples of the foaming agent encompass (hydrogen)carbonate, carbon dioxide, an azo compound, an inert organic solvent, etc. Examples of the hydrophilic polymer encompass starch-cellulose, a starch-cellulose derivative, polyvinyl alcohol, polyacrylic acid (salt), a cross-linked polyacrylic acid (salt) of, e.g., a water absorbent resin, etc. An example of the chain transfer agent is hypophosphoric acid (salt). Each of the above additives can be contained in an amount which is determined as appropriate within a range in which an advantage of the present invention is not impaired. Specifically, with respect to 100 parts by mass of the monomer, the foaming agent is preferably contained in an amount which is not more than 30 parts by mass, the hydrophilic polymer is preferably contained in an amount which is not more than 30 parts by mass, and the chain transfer agent is preferably contained in an amount which is 1 part by weight.

During the polymerizing step, a polymerization initiator is added to the monomer aqueous solution. The polymerization initiator contains a radical which acts to accelerate the polymerization of the monomer. The polymerization initiator is not particularly limited to a specific one. It is thus possible to select, depending on, e.g., a kind of the monomer component to be polymerized and a polymerization condition, one or more from among polymerization initiators used for a polymerization of a normal water absorbent resin. Specifically, a pyrolytic initiator or a photolytic initiator is used. The pyrolytic initiator is not particularly limited to a specific one. Examples of the pyrolytic initiator encompass: persulfates such as sodium persulfate, potassium persulfate, ammonium persulfate, etc.; peroxides such as hydrogen peroxide, t-butyl peroxide, methyl ethyl ketone peroxide, etc.; and azo compounds such as azonitrile compound, azoamidin compound, cyclic azoamidin compound, azoamide compound, alkyl azo compound, 2,2'-azobis(2-amidinopropane)dihydro chloride, 2,2'-azobis[2-(2-imidazoline-2-yl)propane]dihydro chloride, etc. The photolytic initiator is not particularly limited to a specific one. Examples of the photolytic initiator encompass: a benzoin derivative, a benzyl derivative, an acetophenone derivative, a benzophenone derivative, an azo compound, etc. Among the above polymerization initiators, in view of a low cost and a reduction in amount of a residual monomer, the pyrolytic initiator is preferable, and a water-soluble pyrolytic polymerization initiator, particularly a persulfate, is more preferable. Two or more of the above polymerization initiators can be used in combination.

The present invention allows a reduction in retention amount and storage amount of the polymerization initiator solution. This makes it possible to reduce temporal decomposition and degradation of the polymerization initiator solution. As a result, it is possible to stabilize properties of the particulate water absorbing agent to be obtained. This effect is best achieved particularly for a huge-scale continuous production. In view of this, most preferable among the above polymerization initiators is a water-soluble pyrolytic polymerization initiator used in combination with a reducing agent according to need. The water-soluble pyrolytic polymerization initiator is not particularly limited to a specific one. Examples of the water-soluble pyrolytic polymerization initiator encompass: persulfates, hydrogen peroxides, water-soluble azo initiators, etc. Among these, persulfates are preferable. The reducing agent can suitably be a water-soluble one of reducing agents listed below.

The combinational use of the reducing agent can accelerate decomposition of the above polymerization initiators. Thus, it is possible to obtain a redox initiator by combining the reducing agent and one of the polymerization initiators. The reducing agent is not particularly limited to a specific one. Examples of the reducing agent encompass: sulfurous acid (salt) (or bisulfite) such as sodium sulfite, sodium hydrogen sulfite, etc; L-ascorbic acid (salt); reducing metal (salt) such as ferrous salt, etc; and amines, etc.

Each of (i) the polymerization initiator used during the polymerizing step and (ii) the reducing agent used during the polymerizing step according to need is preferably contained in an amount which falls within a range from 0.001 to 2 parts by mass, and more preferably within a range from 0.01 to 0.5 part by mass, with respect to 1 mole of the monomer. It is possible to reduce the amount of a residual monomer in the case where each of the polymerization initiator and the reducing agent, which is used according to need, is contained in an amount which is not less than 0.001 part by mass. Further, it is possible to reduce a water-soluble content of the water absorbent resin in the case where each of the polymerization initiator and the reducing agent, which is used according to need, is contained in an amount which is not more than 2 parts by mass.

During the polymerizing step of the present invention, the monomer is polymerized by emitting an activating energy ray such as a radioactive ray, an electron ray, an ultraviolet ray, etc., to the monomer, instead of adding the polymerization initiator.

The polymerization initiator is normally dissolved in water for use. In this case, the aqueous solution preferably has a polymerization initiator concentration which falls within a range from 1 to 25 mass %, more preferably within a range from 1 to 15 mass %, and particularly preferably within a range from 1 to 5 mass %. It is possible to stabilize the properties of the particulate water absorbing agent to be obtained, by setting the polymerization initiator concentration of the aqueous solution within one of the above ranges. If the polymerization initiator concentration of the aqueous solution is less than 1 mass %, a large amount of the polymerization initiator aqueous solution will be used. This will increase a water concentration of the hydrogel to be obtained. As a result, a large amount of energy will be necessary to dry the hydrogel, thereby increasing a cost. If the polymerization initiator concentration of the aqueous solution is more than 25 mass %, the polymerization initiator will not be sufficiently diffused in the monomer aqueous solution. This will decrease stability of the properties of the particulate water absorbing agent to be obtained.

A polymerization device preferably used in the present invention is a kneader polymerization device or a belt polymerization device. Polymerization methods involving use of a kneader polymerization device are disclosed in U.S. Pat. Nos. 6,867,269, 6,987,151, and 6,710,141. The belt polymerization device includes an endless belt having dams at respective sides. The endless belt is made of steel having a surface coated with fluorine resin. A mixture solution of the monomer aqueous solution and the polymerization initiator aqueous solution is continuously fed onto the endless belt so as to carry out aqueous solution polymerization. This method is referred to as "belt polymerization". Polymerization methods involving use of a belt polymerization device are disclosed in, for example, U.S. Pat. Nos. 4,893,999, 6,241,928, and U.S. Patent Application No. 2005/215734.

There has conventionally been a serious problem that a variation is caused in a polymerization starting period (induction period) and/or a polymerization period in the case where the above polymerization devices are used for a continuous polymerization. In view of this, the inventors of the present invention have conducted a search for a cause of the variation by studying possible factors such as an impurity contained in raw materials and unevenness in temperature of the raw materials. The inventors have consequently found that the cause is a slight variation or change (e.g., concentration decrease due to natural decomposition) in the polymerization initiator concentration of the aqueous solution. Implementing the present invention allows a continuous belt polymerization and a continuous kneader polymerization to be stably carried out.

In the present invention, temperatures during the polymerization (i.e., a polymerization starting temperature and a maximum reached temperature) are determined as appropriate according to, e.g., a kind of the monomer component and a kind of the polymerization initiator. The temperatures are thus not particularly limited to specific ones. The temperatures preferably range from 10 to 140° C., and more preferably from 20 to 120° C. It is possible to shorten a polymerization period and thus improve productivity in the case where a temperature (polymerization starting temperature) during the polymerization is not less than 10° C. It is possible to improve the properties of the water absorbing agent to be obtained, in the case where a temperature (maximum reached temperature) during the polymerization is not more than 140° C. The polymerization period is also determined as appropriate according to, e.g., the kind of the monomer component, the kind of the polymerization initiator, temperature, etc. The polymerization period is thus not particularly limited to a specific one. The polymerization period preferably falls within a range from 0.1 minute to 10 hours, and more preferably within a range from 1 minute to 1 hour. Further, the polymerizing step can be carried out under atmospheric pressure, reduced pressure, or increased pressure.

[Drying Step]

The drying step of the present invention is a step in which the hydrogel (referred to also as "hydrogel polymer") obtained through the above polymerizing step is dried. The hydrogel obtained through the polymerizing step is normally preferably pulverized into particles having a size which falls within an approximate range from 0.1 to 5 mm, before being fed to the drying step. The drying step can be carried out by employing various drying methods. For example, it is possible to employ a method, such as hot air drying and azeotropic dehydration, which involves use of a dryer or a heating furnace. In view of a drying efficiency and prevention of degradation of the hydrogel, the drying step is preferably carried out at a temperature which falls within a range from 80 to 300° C., more preferably within a range from 100 to 250° C., even more preferably within a range from 120 to 220° C., and particularly preferably within a range from 150 to 200° C. A drying period of the drying step is not particularly limited to a specific one, and can thus be determined as appropriate so that a dried polymer to be obtained will have a desired solid content ratio. The polymer obtained through the drying step preferably has a solid content ratio (amount of the polymer remaining after 3 hours of heating at 180° C.) of not less than 80 weight %, and more preferably not less than 90 weight %, for ease of pulverization. In general, the drying period preferably falls within a range from 15 minutes to 2 hours in view of a production efficiency, even though the drying period may vary depending on, e.g., a particle diameter of the hydrogel, the drying temperature, and an amount of air for the drying.

[Pulverizing Step]

The pulverizing step of the present invention is a step in which the hydrogel or the polymer (referred to also as "dried polymer") obtained through the drying step is pulverized. This pulverization allows water absorbent resin particles to be obtained. The pulverization is preferably carried out so as to obtain as large a number as possible of water absorbent resin particles having a desired particle diameter (preferably having a weight average particle diameter which falls within a range from 200 to 800 µm). The pulverization is not particularly limited in method. Thus, it is possible to employ a conventionally known method.

[Classifying Step]

The classifying step of the present invention is a step in which the water absorbent resin particles obtained through the above pulverizing step are classified. During the classifying step, the water absorbent resin particles are sieved so as to select particles each having a desired particle diameter (preferably having a weight average particle diameter which falls within the range from 200 to 800 µm). As a result, a target particulate water absorbing agent is obtained. The classification is not particularly limited in method. Thus, it is possible to employ a conventionally known method. Note that the weight average particle diameter is measured by a method disclosed in U.S. Patent Application No. 2006/0204755.

[Fine Powder Recycling Step]

A fine powder recycling step of the present invention is a step in which fine powder (e.g., particles which have passed through a sieve having a mesh size of 150 µm) produced during the pulverizing step or when the particle size is adjusted during the classifying step is returned to the polymerizing step or the drying step. The fine powder recycling step is not essential. Whether or not the fine powder recycling step needs to be carried out depends on the properties of a target particulate water absorbing agent.

[Surface Cross-Linking Step]

The surface cross-linking step of the present invention is a step in which the water absorbent resin particles obtained through the above classifying step are cross-linked in a vicinity of their surfaces with use of a surface cross-linking agent. The present invention is suitably applicable in a case where a modifier to be used is a surface cross-linking agent. The water absorbent resin particles each internally have a cross-linked structure. In view of prevention of agglomeration, the individual water absorbent resin particles are further cross-linked so that their surfaces or the vicinity of the surfaces will have a cross-linking density which is higher than an internal cross-linking density. Note that the phrase "surfaces or the vicinity of the surfaces" stands for a surface layer and normally corresponds to a portion having a thickness of not more than tens of micrometers or of not more than $\frac{1}{10}$ of a particle radius. The thickness is, however, determined as appropriate according to an application.

The surface cross-linking of the present invention is not particularly limited in method. The following lists example methods:

(1) Method in which an organic surface cross-linking agent and/or a water-soluble inorganic surface cross-linking agent is/are used
(2) Method in which a cross-linking monomer is cross-linked and polymerized with the water absorbent resin particles in their surfaces (e.g., method disclosed in the specification of U.S. Pat. No. 7,201,941)
(3) Method in which the water absorbent resin particles are radically cross-linked with use of, for example, a persulfate (e.g., method disclosed in the specification of U.S. Pat. No. 4,783,510)

In view of productivity, the cross-linking reaction is preferably accelerated by heating or irradiation with a radioactive ray (preferably a ultraviolet ray disclosed in the specification of European Patent No. 1,824,910). It is possible to achieve an excellent absorbency against pressure, i.e., to increase an absorption capacity under pressure, by surface-cross-linking the water absorbent resin particles in their surfaces or the vicinity of the surfaces.

The term "surface cross-linking" according to the present invention stands for surface-cross-linking achieved when water absorbent resin particles are chemically or physically modified in regions corresponding to the surfaces or the vicinity of the surfaces. In a case of, e.g., a partially neutralized cross-linked polyacrylic acid, its chemical modification means surface cross-linking achieved with use of an organic surface cross-linking agent (e.g., polyhydric alcohol, polyvalent glycidyl compound, polyvalent amine, etc) which has two or more functional groups that are reactive to a functional group (particularly a carboxyl group) present in the vicinity of the particle surfaces. Other than this example, the surface cross-linking of the present invention also encompasses, for example, surface cross-linking achieved by means of an ionic bond formed by a polyvalent metal such as trivalent aluminum with the surface carboxyl group. In the present invention, linkage in the surface cross-linking is not particularly limited in form. The water absorbent resin particles which are cross-linked in their surfaces or the vicinity of the surfaces are used to produce a particulate water absorbing agent.

The surface cross-linking agent used during the surface cross-linking step is not particularly limited to a specific one. Examples of the surface cross-linking agent encompass: (i) polyhydric alcohol compounds such as ethylene glycol, diethylene glycol, propylene glycol, triethylene glycol, tetraethylene glycol, polyethylene glycol, 1,3-propane diol, dipropylene glycol, 2,2,4-trimethyl-1,3-pentane diol, polypropylene glycol, glycerin, polyglycerin, 2-butene-1,4-diol, 1,4-butandiol, 1,5-pentane diol, 1,6-hexanediol, 1,2-cyclohexanedimethanol, 1,2-cyclohexanediol, trimethylolpropane, diethanolamine, triethanolamine, polyoxypropylene, oxyethylene-oxypropylene block copolymer, pentaerythritol, sorbitol, etc; (ii) epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, glycidol, etc; (iii) polyamine compounds and their inorganic salts or organic salts (e.g., aziridinium salt), the polyamine compounds including ethylenediamine, diethylenetriamine, triethylenetetramine, tetraethylenepentamine, pentaethylenehexamine, polyethylene imine, etc; (iv) polyvalent isocyanate compounds such as 2,4-tolylene diisocyanate, hexamethylene diisocyanate, etc; (v) polyvalent oxazoline compounds such as 1,2-ethylenebisoxazoline, etc; (vi) alkylenecarbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxy methyl-1,3-dioxolane-2-one, 1,3-dioxane-2-one, 4-methyl-1,3-dioxane-2-one, 4,6-dimethyl-1,3-dioxane-2-one, 1,3-dioxopan-2-one, etc; (vii) haloepoxy compounds such as epichlorohydrin, epibromhydrin, α-methyl epichlorohydrin, etc; (viii) compounds (e.g., a hydroxide, a chloride, etc) of polyvalent metals such as zinc, calcium, magnesium, aluminum, iron, zirconium, etc; (ix) oxazolidinone compounds such as 2-oxazolidinone, etc. (exemplified in U.S. Pat. No. 6,559,239); (x) oxetane compounds; and (xi) cyclic urea compounds. Among these, polyhydric alcohol compounds, epoxy compounds, polyamine compounds (and their salts), alkylenecarbonate compounds and oxazolidinone compounds are preferable. Two or more kinds of the above surface cross-linking agents can be used in combination.

Either a single kind or more than one kind of dehydration surface cross-linking agent can be selected, as a modifier for use in the surface cross-linking step, from the group consisting of oxazolidinone compounds, alkylenecarbonate compounds, polyhydric alcohol compounds, and oxetane compounds, all of which are mentioned as examples of the surface cross-linking agent. Among these, it is preferable to use a polyhydric alcohol compound. Another surface cross-linking agent (e.g., oxazolinone compound) can be used in combination according to need. The above dehydration surface cross-linking agents are highly safe and allow production of a particulate water absorbing agent having high properties. The polyhydric alcohol is preferably a polyhydric alcohol having 2 to 10 carbon atoms, and more preferably a polyhydric alcohol having 3 to 8 carbon atoms.

In contrast, use of a surface cross-linking agent having a low reactivity requires a high-temperature dehydration reaction (e.g., an esterification reaction or amidation reaction between the carboxyl group of the water absorbent resin and the surface cross-linking agent). As such, properties of a particulate water absorbing agent to be obtained have conventionally been unstable. Further, a decrease in the properties of the particulate water absorbing agent has been more likely particularly on a machine level (continuous production of not less than 1000 kg/hr) than on a small scale or on a laboratory scale. The present invention solves this problem and thus allows a stable production of a particulate water absorbing agent which has high properties and high safety.

During the surface cross-linking step of the present invention, a plurality of surface cross-linking agents are preferably added as a modifier either simultaneously or separately. Example combinations of the plurality of surface cross-linking agents encompass: a combination of different dehydration surface cross-linking agents; and a combination of a dehydration surface cross-linking agent and an ionic bonding surface cross-linking agent. The plurality of surface cross-linking agents can be added either simultaneously or separately, and also can be added either in one portion or in separate portions.

The ionic bonding surface cross-linking agent is not particularly limited to a specific one, and is preferably, for example, a polyvalent metal salt or hydroxide described later. The combinational use of the plurality of surface cross-linking agents allows an improvement in properties such as liquid permeability (SFC).

Conventionally, in the case where a plurality of surface cross-linking agents are used, even if each individual surface cross-linking agent has only a slight property variation, there has occurred a large variation when the plurality of surface cross-linking agents are used in combination. This has occasionally caused a property decrease in a product obtained. The present invention solves this problem and thus allows a production of a particulate water absorbing agent having high properties. In other words, the present invention achieves a greater advantage in the case where a plurality of surface cross-linking agents or dehydration surface cross-linking agents are used as a modifier.

The surface cross-linking agent is preferably contained in an amount which falls within a range from 0.001 to 10 parts by mass, and more preferably within a range from 0.01 to 5 parts by mass, with respect to 100 parts by mass of the solid content of the polymer (water absorbent resin particles). The cross-linking density in the vicinity of the surfaces of the water absorbent resin particles can be made higher than the internal cross-linking density by containing the surface cross-linking agent in an amount which falls within one of the above ranges. It will be undesirably uneconomical to contain the surface cross-linking agent in an amount which exceeds 10 parts by mass. On the other hand, properties, such as absorbency against pressure, of the water absorbing agent will undesirably not be sufficiently improved in the case where the surface cross-linking agent is contained in an amount which is less than 0.001 part by mass.

During the surface cross-linking step, the water absorbent resin particles and the surface cross-linking agent are mixed. It is preferable to use water as a solvent. A use amount of the water, which use amount depends on, e.g., a kind, particle diameters, and water content of the water absorbent resin particles, preferably falls within a range from 0.01 to 20 parts by mass, and more preferably within a range from 0.5 to 10 parts by mass, with respect to 100 parts by mass of the solid content of the water absorbent resin particles. In this aqueous solution, a hydrophilic organic solvent can be mixed according to need. Examples of the hydrophilic organic solvent encompass: lower alcohols such as methyl alcohol, ethyl alcohol, n-propyl alcohol, isopropyl alcohol, n-butyl alcohol, isobutyl alcohol, t-butyl alcohol, etc;

ketones such as acetone, etc; ethers such as dioxane, tetrahydrofuran, etc; amides such as N,N-dimethylformamide, etc; and sulfoxides such as dimethyl sulfoxide, etc. The hydrophilic organic solvent is preferably contained in an amount which is not more than 20 parts by mass, and more preferably not more than 10 parts by mass, with respect to 100 parts by mass of the solid content of the water absorbent resin particles.

In the present invention, an aqueous solution of the surface cross-linking agent (surface cross-linking agent aqueous solution) preferably has a concentration which falls within a range from 5 to 50 mass %, and more preferably within a range from 10 to 40 mass %. By setting the surface cross-linking agent concentration of the aqueous solution within one of the above ranges, it is possible not only to preferably stabilize the properties and increase the cross-linking density of the water absorbing agent to be obtained, but also to preferably reduce viscosity of the aqueous solution so that the surface cross-linking agent is uniformly dispersed. In a case where two or more kinds of surface cross-linking agents are used, a sum of their respective concentrations is set within one of the above ranges.

A method for adhering the surface cross-linking agent aqueous solution to the surfaces of the water absorbent resin particles is not particularly limited to a specific one. Examples of the method to be employed encompass: a method in which the surface cross-linking agent aqueous solution is sprayed; and a method in which the surface cross-linking agent aqueous solution is dropped. Of these two methods, the spraying method is preferable because it allows the surface cross-linking agent to be uniformly adhered. Sprayed droplets preferably have an average particle diameter which falls within a range from 0.1 to 300 µm, and more preferably within a range from 0.1 to 200 µm.

The surface cross-linking agent can be reacted with the water absorbent resin particles either at room temperature or at high temperature. The reaction is, however, preferably carried out at high temperature. In the present invention, a treatment in which a reaction is carried out at high temperature is referred to as "heat treatment". An atmospheric temperature during the heat treatment is not particularly limited to a specific one, and preferably falls within a range from 80 to 250° C., more preferably within a range from 100 to 250° C., and particularly preferably within a range from 150 to 250° C. (These temperature ranges particularly preferably apply to a case in which the dehydration esterification surface cross-linking agent is used.) By setting the atmospheric temperature during the heat treatment within one of the above ranges, it is possible not only to achieve uniform surface cross-linking and thus secure a high productivity, but also to prevent degradation of the water absorbent resin particles. The heat treatment is preferably carried out for a period which falls within a range from 1 minute to 2 hours. The heat treatment can be carried out either while the particles are settled or while the particles are being stirred.

[Cooling Step]

The cooling step of the present invention is a step optionally carried out after the surface cross-linking step. The cooling step is a step in which, for example, cooling is carried out with respect to a particulate water absorbing agent obtained by heating the water absorbent resin particles so that the particles are cross-linked in the vicinity of their surfaces during the above surface cross-linking step. A cooling device used during the cooling step is not particularly limited to a specific one. Examples of the cooling device encompass a two-shaft stirring dryer, exemplified in, e.g., U.S. Pat. No. 6,378,453, in which cooling water is flown through an inside of a heat transfer surface such as an inner wall.

[Additive Adding Step]

The present invention can further include a step of adding a modifier (additive) other than the above surface cross-linking agent to the water absorbent resin particles. The additive adding step is preferably carried out after the polymerizing step, and more preferably after the drying step. The additive can also be added during a step such as the surface cross-linking step and the cooling step. The modifier (additive) is at least one selected from a surface cross-linking agent, a surface active agent, a chelating agent, a deodorant agent, an antibacterial agent, a reducing agent, and an anti-coloring agent.

The present invention is suitably applicable in a case where the modifier (additive) is added in a form of a solution, particularly an aqueous solution, together with or separately from the surface cross-linking agent. Specifically, after the modifier (additive) solution is prepared so as to have a predetermined concentration, the solution can be diluted by the above method. The modifier to be added after the surface cross-linking is used during the above step (a) in addition to the above surface cross-linking agent serving as a modifier.

Examples of the additive encompass (A) a deodorant component, (B) a polyvalent metal salt, (C) inorganic particles (including (D) composite hydrous oxide particles), (E) a chelating agent, and (F) other additives. Adding these additives can impart various functions to the water absorbing agent. As in the case of the polymerization initiator and the surface cross-linking agent, the method of the present invention is preferably applicable in a case where the modifier (additive) is added in the form of a solution or a dispersion solution, particularly an aqueous solution. In this case, it is possible to improve or stabilize the properties of the particulate water absorbing agent to be obtained. The solution has a concentration which is selected as appropriate from a range of levels including those not below a saturation concentration. The concentration normally preferably falls within a range from 0.1 to 90 mass %, and more preferably within a range from 1 to 50 mass %.

(A) Deodorant Component

A particulate water absorbing agent obtained by the production method of the present invention can contain a deodorant component, preferably a plant component, so as to have a deodorant property. The plant component is preferably either one compound or two or more compounds selected from polyphenols, flavones, and caffeine. The plant component is particularly preferably either one compound or two or more compounds selected from tannin, tannic acid, galla, gallnut, and gallic acid. Other plant components can be added instead. Such other plant components encompass, for example: a component derived from a theaceous plant such as camellia, Eurya japonica, Ternstroemia gymnanthera, etc; a component derived from a poaceous plant such as rice plant, bamboo grass, bamboo, corn, and wheat (or barley, oat, etc.); and a component derived from a rubiaceous plant such as coffee, etc. The plant component can be in a form of either an extract (essential oil) or a plant itself. Alternatively, the particulate water absorbing agent can contain a plant residue, extract residue or the like produced as a by-product during a production process in a plant processing industry or a food processing industry.

(B) Polyvalent Metal Salt

The particulate water absorbing agent obtained by the production method of the present invention can contain either a polyvalent metal salt or a hydroxide, particularly a polyvalent metal salt, in order to improve a liquid permeability and fluidity of the water absorbent resin particles. The polyvalent metal salt thus added also reduces blocking which occurs when the water absorbent resin particles absorb moisture. The polyvalent metal also acts as an ionic bonding surface cross-linking agent and thus contributes to improvement in liquid permeability. The polyvalent metal salt can thus be used in combination with the above covalent bonding surface cross-linking agent, and can be added simultaneously with or separately from the covalent bonding surface cross-linking agent. Note that the polyvalent metal salt can also be used as a surface cross-linking agent in a case where the polyvalent metal can be reacted with the water absorbent resin.

Examples of the polyvalent metal salt encompass an organic polyvalent metal salt and an inorganic polyvalent metal salt. Preferably examples of the inorganic polyvalent metal salt encompass aluminum chloride, polyaluminum chloride, aluminum sulfate, aluminum nitrate, bis aluminum potassium sulfate, bis aluminum sodium sulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, zirconium nitrate, etc. Preferable among these are the aluminum compounds (aluminum chloride, polyaluminum chloride, aluminum sulfate, aluminum nitrate, bis aluminum potassium sulfate, bis aluminum sodium sulfate, potassium alum, ammonium alum, sodium alum, sodium aluminate, etc). Particularly preferable among these compounds is aluminum sulfate. Most preferable is hydrated crystal powder of, e.g., aluminum sulfate octadecahydrate or aluminum sulfate hydrate (tetradecahydrate to octadecahydrate). A single kind of the above polyvalent metal salts can be used independently, or alternatively, two or more kinds of the above polyvalent metal salts can be used in combination. The polyvalent metal salt is preferably used in a form of a solution, particularly preferably in a form of an aqueous solution, because the polyvalent metal salt in the above form is easy to handle and has a good mixing property with respect to the particulate water absorbing agent.

Examples of the organic polyvalent metal salt are disclosed in the specification of U.S. Pat. No. 7,282,262 and the specification of U.S. Patent Application No. 2006/0073969. The organic polyvalent metal salt used in the present invention is preferably a polyvalent metal salt having in a single molecule not fewer than 7 carbon atoms. Particularly preferable is a long-chain fatty acid having in a single molecule not fewer than 12 carbon atoms and having no unsaturated bond. Examples of the fatty acid encompass lauric acid, myristic acid, palmitic acid, and stearic acid.

The polyvalent metal salt is preferably in a form of particles. Specifically, in view of a mixing property, the polyvalent metal salt is preferably in a form of particles having particle diameters which are smaller than those of the water absorbent resin particles. The polyvalent metal salt particles preferably have a mass average particle diameter of not more than 500 μm, and more preferably not more than 400 μm. The polyvalent metal salt particles include particles, each having a particle diameter of not more than 150 μm, at a ratio of not less than 20 mass %, and more preferably not less than 30 mass %.

The polyvalent metal salt is preferably in a form of an aqueous solution to be mixed with the water absorbent resin particles. In a case where the aqueous solution has a high concentration, it is possible to prevent polyvalent metal ions from permeating or diffusing into the individual water absorbent resin particles. In view of this, the aqueous solution preferably has a concentration of not less than 50%, more preferably not less than 60%, even more preferably not less than 70%, still more preferably not less than 80%, and particularly preferably not less than 90%, with respect to a saturation concentration. Alternatively, the aqueous solution can have its saturation concentration or can be a dispersion solution having a concentration higher than the saturation concentration.

(C) Inorganic Particles

The particulate water absorbing agent obtained by the production method of the present invention can contain inorganic particles, particularly water-insoluble inorganic particles, in order to prevent blocking which occurs when the water absorbent resin particles absorb moisture. The inorganic particles used in the present invention are not particularly limited to a specific kind. Examples of the inorganic particles encompass: particles of a metal oxide such as silicon dioxide, titanium oxide, etc; a silicic acid (salt) such as natural zeolite, synthetic zeolite, etc; kaolin; talc; clay; and bentonite. Preferable among these are particles of silicon dioxide or silicic acid (salt). More preferable are particles of silicon dioxide or silicic acid (salt) which particles have an average particle diameter which falls within a range from 0.001 to 200 μm as measured by a Coulter counter method.

(D) Composite Hydrous Oxide Particles

The above inorganic particles can include particles of a composite hydrous oxide. These particles improve the fluidity and deodorant capability of the particulate water absorbing agent. Examples of the composite hydrous oxide used in the present invention encompass: a composite hydrous oxide containing zinc and silicon; and a composite hydrous oxide containing zinc and aluminum.

(E) Chelating Agent

The water absorbing agent obtained by the production method of the present invention can contain a chelating agent.

The chelating agent thus added increase absorbency of the water absorbing agent with respect to a body fluid such as urine, etc. The chelating agent is not particularly limited to a specific one. Examples of the chelating agent encompass a polymer chelating agent and a non-polymer chelating agent. Particularly preferable is an acid group-containing non-polymer chelating agent. The number of the acid group contained in the acid group-containing non-polymer chelating agent preferably falls within a range from 2 to 100, more preferably within a range from 2 to 50, and particularly preferably within a range from 2 to 10. Preferable examples of the acid group encompass a phosphate group and a carboxylic acid group. Other preferable chelating agents are an amino carboxylic acid chelating agent and an amino phosphoric acid chelating agent, each of which contains nitrogen in its individual molecules. Specific examples of preferable chelating agents encompass: aminocarboxylic acid metal chelating agents such as iminodiacetic acid, hydroxyethyl iminodiacetic acid, nitrilotriacetic acid, nitrilotripropionate, ethylenediamine tetraacetic acid, hydroxyethylenediamine triacetic acid, hexamethylenediamine tetraacetic acid, diethylenetriamine pentaacetic acid, triethylenetetramine hexaacetic acid, trans-1,2-diaminocyclohexane tetraacetic acid, bis(2-hydroxyethyl) glycine, diaminopropanol tetraacetic acid, ethylenediamine-2-propionate, glycol ether diaminetetraacetic acid, bis(2-hydroxy benzyl)ethylenediamine diacetic acid, and a salt of any of the above; and phosphorus compounds such as ethylenediamine-N,N'-di(methylene phosphinic acid), ethylenediamine tetra(methylene phosphinic acid), nitriloacetic acid-di(methylene phosphinic acid), nitrilodiacetic acid-(methylene phosphinic acid), nitriloacetic acid-β-propionate-methylene phosphonic acid, nitrilotris(methylene phosphonic acid), cyclohexanediamine tetra(methylene phosphonic acid), ethylenediamine-N,N'-diacetic acid-N,N'-di(methylene phosphonic acid), ethylenediamine-N,N'-di(methylene phosphonic acid), ethylenediamine tetra(methylene phosphonic acid), polymethylenediamine tetra(methylene phosphonic acid), diethylenetriamine penta(methylene phosphonic acid), 1-hydroxyethylidene diphosphonic acid, and salts of the above. The chelating agent to be used can be added to a monomer or a monomer aqueous solution.

(F) Other Additives

The water absorbent resin particles can contain additives other than the above additives according to need. Such other additives include a disinfectant, an antibacterial agent, a fragrant material, a foaming agent, a pigment, a dye, a hydrophilic short fiber, a fertilizer, an oxidizing agent, a reducing agent, a surface active agent, an anti-coloring agent, an aqueous salt, etc. The reducing agent is preferably an inorganic reducing agent containing sulfur or phosphorus, and can, for example, be a reducing agent disclosed in, e.g., U.S. Patent Application No. 2006/74160. The surface active agent can, for example, be one disclosed in U.S. Pat. No. 6,599,989. The anti-coloring agent is, for example, an organic or inorganic anti-coloring agent.

Each of the above additives and modifiers is contained in an amount which is determined as appropriate according to an application and a kind of the additive or modifier. The amount of each additive above is normally preferably not more than 10 parts by mass, more preferably falls within a range from 0.0001 to 5 parts by mass, and particularly preferably falls within a range from 0.002 to 3 parts by mass, with respect to 100 parts by mass of the solid content of the polymer (water absorbent resin particles). In the case where the chelating agent is added, the amount of each additive above is preferably not less than 0.0005 part by mass, more preferably not less than 0.001 part by mass, even more preferably not less than 0.05 part by mass, and particularly preferably not less than 0.1 part by mass, with respect to 100 parts by mass of the water absorbent resin particles. The chelating agent is preferably contained in an amount which is not more than 1.0 part by mass, more preferably not more than 0.5 part by mass, and particularly preferably not more than 0.2 part by mass.

Additives preferable in terms of liquid permeability are a polymeric polyamine and the polyvalent metal salt (B). Of these, the polyvalent metal salt (B) is particularly preferable. After the polyvalent metal salt (B) is added, the polyvalent metal salt (B) and the water absorbent resin particles are preferably mixed. Specific examples of a device for the mixing encompass a cylindrical mixer, a screw type mixer, a screw type extruder, a Turbulizer, a Nauta mixer, a V type mixer, a ribbon-type mixer, a double-arm kneader, a flow-type mixer, an airflow-type mixer, a rotary disk mixer, a roll mixer, a rotational mixer, and a Lodige mixer.

The polyvalent metal salt is preferably in a form of an aqueous solution when added to the water absorbent resin particles. The aqueous solution is added in droplets each having a size adjustable as appropriate. The aqueous solution preferably has a concentration which is not less than 50 mass % with respect to a saturation concentration. By setting the concentration within this range, it is possible to prevent polyvalent metal ions (e.g., aluminum ions) from permeating or diffusing into the individual water absorbent resin particles. In view of this, the concentration is more preferably not less than 60 mass %, even more preferably not less than 70 mass %, still more preferably not less than 80 mass %, and particularly preferably not less than 90 mass %. The aqueous solution can also have a saturation concentration.

[Granulating Step]

The present invention can include a granulating step in which the particle size of the particulate water absorbing agent is readjusted. According to the process of producing the particulate water absorbing agent, although the particle diameters of the water absorbent resin particles are adjusted during the classifying step, the particulate water absorbing agent obtained after the cooling step may include an agglomerate having a large particle diameter. Such an agglomerate needs to be subjected to a pulverization treatment and a classification treatment. The pulverization treatment and the classification treatment are not particularly limited in method, order, or number of performance. One example method is that (i) a classification treatment is first carried out so that agglomerates having large particle diameters are sieved, (ii) the agglomerates are next subjected to a pulverization treatment to obtain smaller particles, and (iii) these particles are then subjected to a further classification treatment. Through this series of operations, it is possible to obtain a particulate water absorbing agent having a desired particle diameter (preferably having a weight average particle diameter which falls within the range from 200 to 800 μm). In view of a production efficiency, the granulating step is preferably carried out after the cooling step. The above granulating method is exemplified in, e.g., U.S. Pat. No. 7,347,330 and U.S. Patent Application No. 2005/0113252.

[Packaging Step]

The granulating step of the present invention can be combined with a packaging step. The packaging step is a step in which the particulate water absorbing agent granulated during the granulating step is packaged. The packaging of the particulate water absorbing agent is not particularly limited in method. One example method is that a particulate water absorbing agent stored in a hopper is transferred, with use of a filling device, to fill a container made of a packaging material. The container made of a packaging material is, for example, a storage bag such as a flexible container bag. In the production method of the present invention, the particulate water absorbing agent packed fully in a flexible container bag undergoes a predetermined inspection before shipment.

Figure 2:
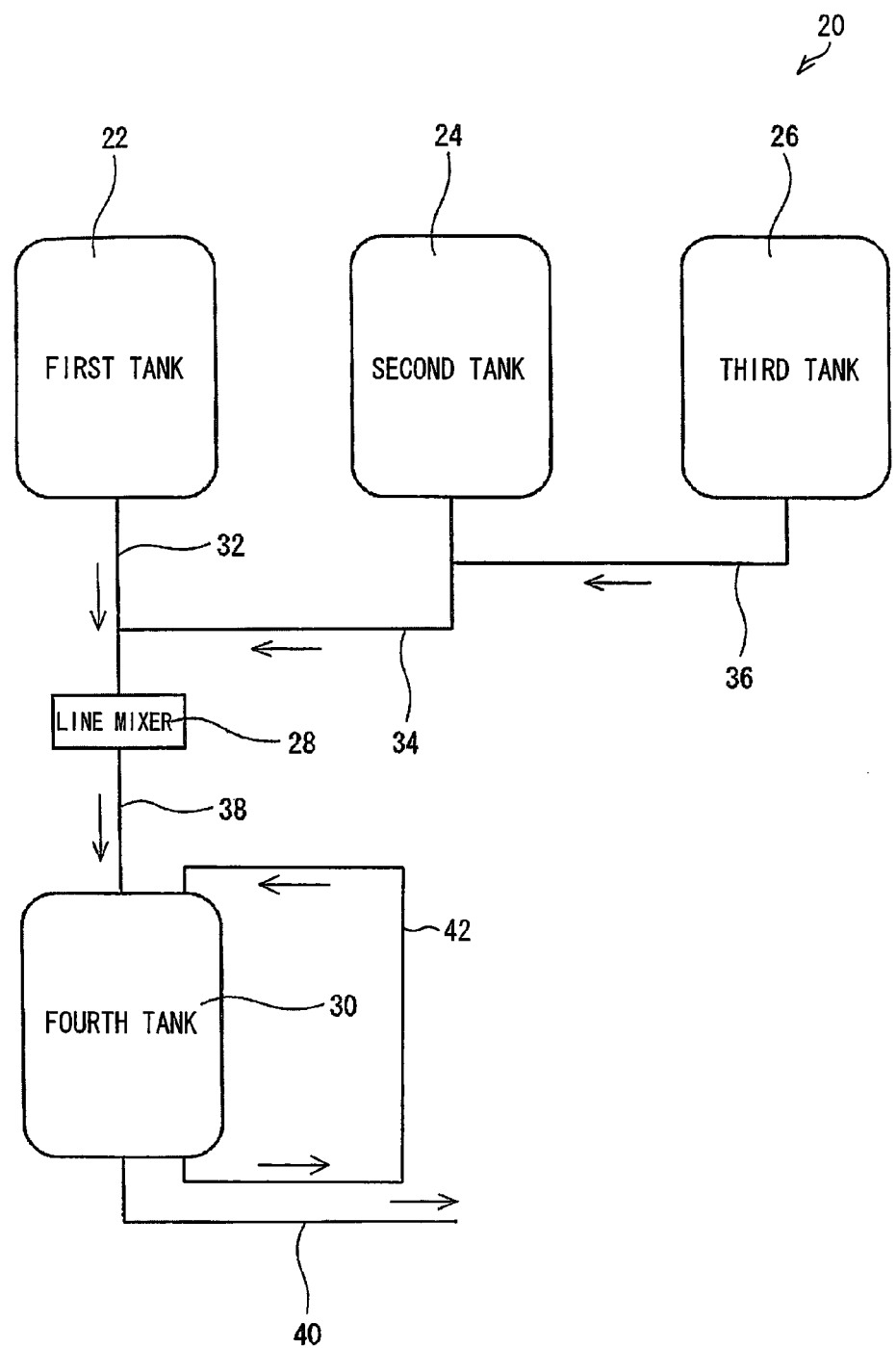
FIG. 2
Figure 3:
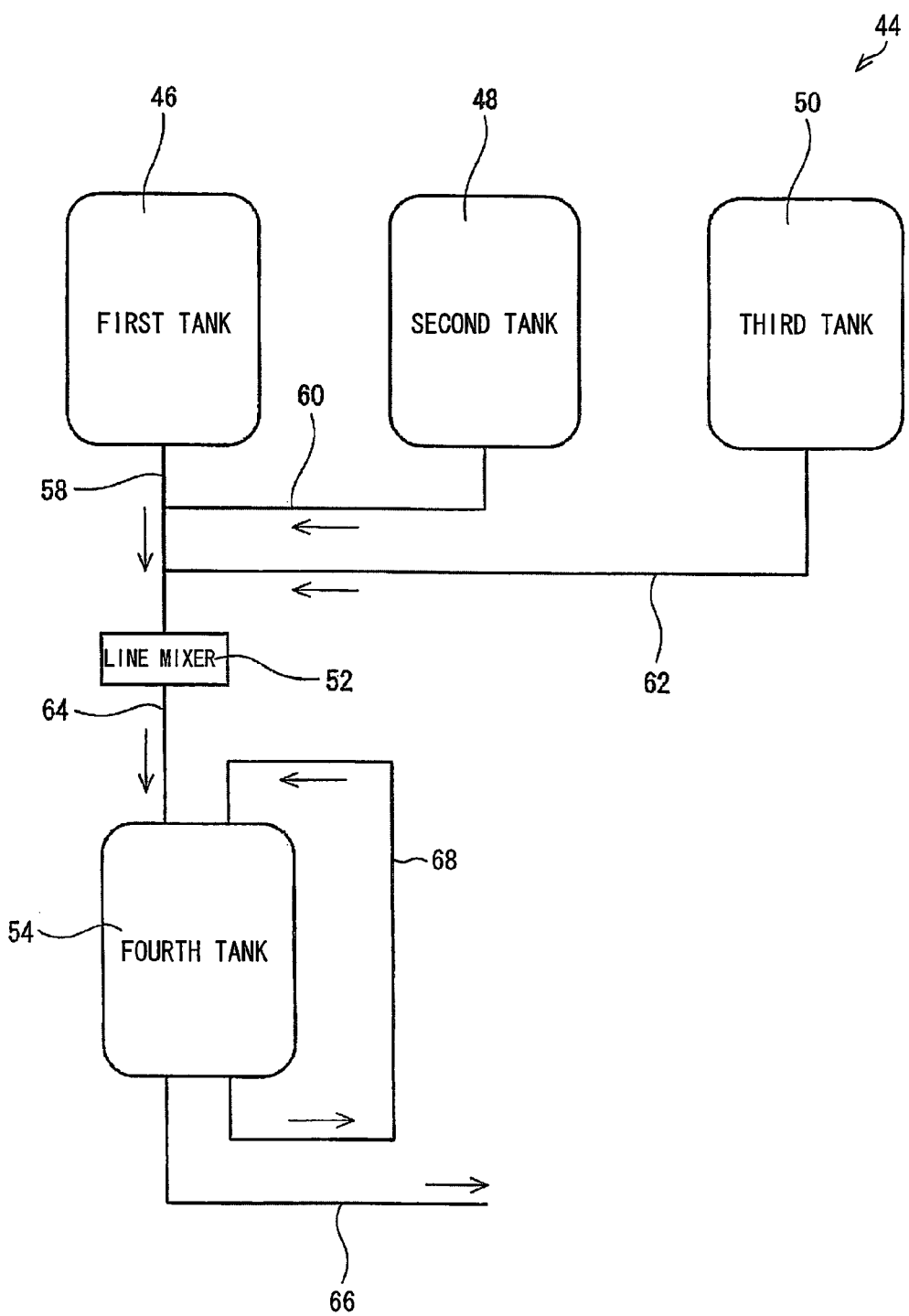
FIG. 3
Figure 4:
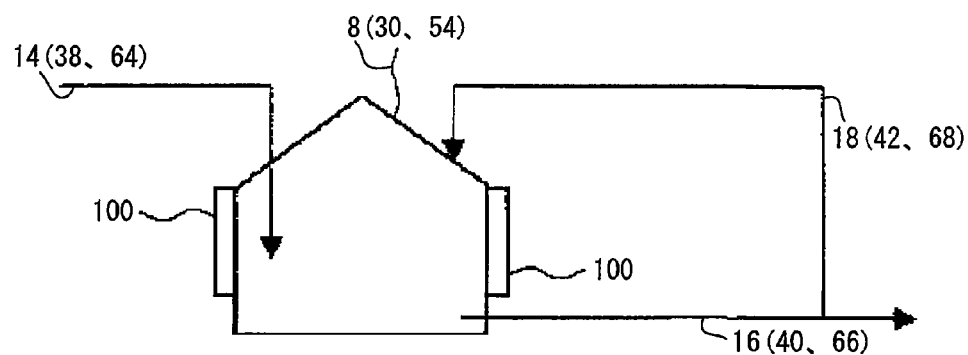
FIG. 4
Figure 5:
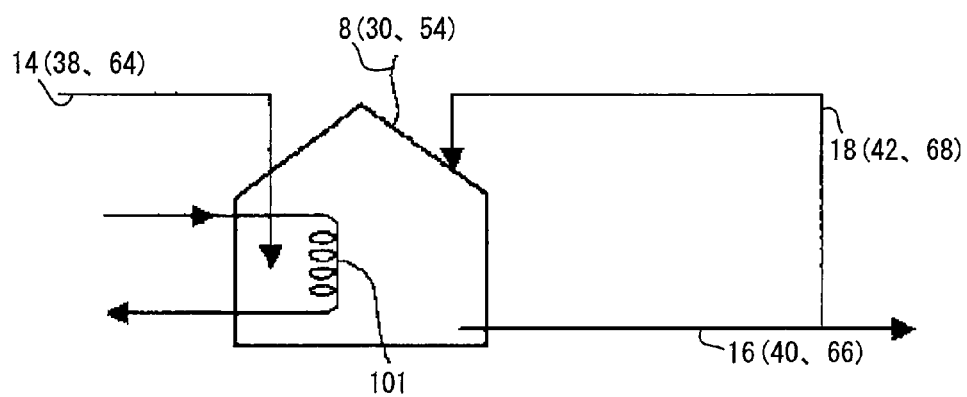
FIG. 5
Figure 6:
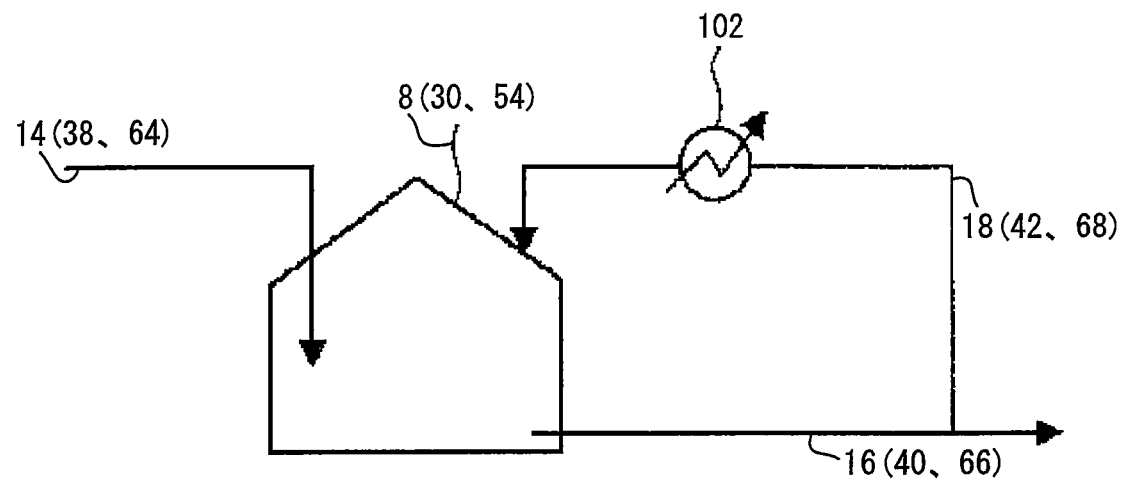
FIG. 6

FIGS. 1 through 3 are each an explanatory diagram schematically illustrating an embodiment of the present invention. Each of FIGS. 1 through 3 is a diagram schematically illustrating an apparatus suitably applicable to steps, included in the production process of the present invention, for preparing, e.g., a polymerization initiator solution, a surface cross-linking agent solution, and an additive solution. FIGS. 4 through 6 are each an explanatory diagram schematically illustrating a method for cooling or heating a liquid in a storage tank after the liquid passes through a line mixer. Neither of the cooling method and the heating method is particularly limited to a specific one. Each of the cooling method and the heating method can be determined as appropriate according to conditions such as (i) properties of a substance to be cooled or heated, (ii) a concentration of a liquid to be prepared, and (iii) a frequency of preparing such a liquid.

The following description deals in detail with the respective steps for preparing a polymerization initiator solution, a surface cross-linking agent solution, and an additive solution.

[Polymerization Initiator Solution Preparing Step]

In the present invention, a polymerization initiator solution can be prepared with use of any of the respective apparatuses illustrated in FIGS. 1 through 3. The description below specifically refers to FIG. 1, illustrating an apparatus which is particularly suitably applicable to the preparation of the polymerization initiator solution of the present invention.

The apparatus 2 illustrated in FIG. 1 includes a first tank 4, a line mixer 6, a second tank 8, a first tube 12, a second tube 14, a third tube 16, and a fourth tube 18 (for a circulation loop). The first tube 12 connects the first tank 4 with the line mixer 6. The second tube 14 connects the line mixer 6 with the second tank 8. The third tube 16 connects the second tank 8 with a next step. The fourth tube 18 branches off from midstream of the third tube 16 and is connected back to the second tank 8. As such, a part of the third tube 16 and the fourth tube 18 together form a circulation loop (hereinafter referred to simply as "circulation loop 1").

The term "circulation loop (closed flow path)" used in the present invention stands for a piping system in which a starting point of a liquid flow is identical to its ending point. Within the circulation loop, an apparatus, such as a tank, a heat exchanger, and/or a pump may be provided. The circulation loop can be a curved circulation loop (i.e., a circulation loop in a narrow sense) or a polygonal circulation loop formed by linear tubes connected to one another. The circulation loop can also include tubes which are arranged three-dimensionally.

First, a polymerization initiator (e.g., sodium persulfate) and water are fed into the first tank 4 in batch so as to prepare a polymerization initiator aqueous solution (mother liquor). During this step, the aqueous solution (mother liquor) in the first tank 4 preferably has a polymerization initiator concentration which falls within a range from 20 to 50 mass %, and more preferably within a range from 25 to 45 mass %. The polymerization initiator is in many cases a solid. The production method of the present invention preferably first uses the polymerization initiator aqueous solution as a mother liquor. The aqueous solution (mother liquor) can have such a high polymerization initiator concentration as a concentration which falls within one of the above ranges. This makes it possible to reduce a capacity of the first tank 4 and thus reduce a space taken up by the apparatus.

Next, the polymerization initiator aqueous solution (mother liquor) prepared in the first tank 4 is continuously taken out via the first tube 12. The polymerization initiator aqueous solution is then diluted with additionally injected water so as to have a desired concentration, and is transferred to the line mixer 6. The polymerization initiator aqueous solution passes through the line mixer 6 and is then continuously poured into the second tank 8 via the second tube 14, so that a predetermined amount of the aqueous solution is stored in the second tank 8. The aqueous solution stored in the second tank 8 is continuously taken out via the third tube 16 and is continuously added to a monomer aqueous solution.

The aqueous solution through the second tube 14 has been found to have an unstable concentration. This is because the polymerization initiator aqueous solution is not sufficiently mixed with the water in the line mixer 6. As such, if the polymerization initiator aqueous solution through the second tube 14 is directly added to a monomer aqueous solution as in conventional cases, a particulate water absorbing agent to be obtained will also have an unstable quality. In view of this, according to the present invention, the polymerization initiator aqueous solution is temporarily stored in the second tank 8 after passing through the second tube 14. This arrangement allows the aqueous solution in the second tank 8 to be circulated via the circulation loop 1 so that the water and the solute are sufficiently mixed with each other.

This method stabilizes the polymerization initiator concentration of the aqueous solution stored in the second tank 8. The polymerization initiator aqueous solution stored in the second tank 8 preferably has a concentration which falls within a range from 1 to 25 mass %, and more preferably within a range from 5 to 20 mass %. The aqueous solution concentration is likely to be stabilized by setting the aqueous solution concentration within one of the above ranges. In addition, since the polymerization initiator aqueous solution through the third tube 16 has a stable concentration, it is possible to produce a high-quality water absorbing agent.

In the case where the polymerization initiator aqueous solution is prepared in batches, the aqueous solution has a low polymerization initiator concentration. This case thus requires a large amount of the aqueous solution. It follows that this case undesirably requires a large-capacity tank. Moreover, in the case where a large amount of the polymerization initiator aqueous solution is used, the aqueous solution is likely subjected to temporal decomposition (concentration decrease) while being stored. This may cause a variation in, e.g., polymerization period.

In view of this, according to the apparatus 2 illustrated in FIG. 1, the polymerization initiator aqueous solution is continuously poured into the second tank 8, while the aqueous solution is continuously taken out from the second tank 8. This allows the apparatus to operate while a liquid surface in the second tank 8 is controlled at a substantially constant level.

Specifically, a ratio of x/y preferably falls within a range from 0.95 to 1.05, where x is an amount of the polymerization initiator aqueous solution poured into the second tank 8, and y is an amount of the polymerization initiator aqueous solution taken out from the second tank 8. It is preferable that (i) a flow rate is controlled for each of the amounts x and y so that the ratio falls within the range, and also (ii) an amount of the polymerization initiator aqueous solution stored in the second tank 8 is controlled so that the amount falls within a range from 10 to 90% of the capacity of the second tank 8. This arrangement allows a reduction in (i) the capacity of the second tank 8 and (ii) a period during which the polymerization initiator aqueous solution is retained in the second tank 8. Note that neither of the amounts x and y includes an amount of the polymerization initiator aqueous solution which is circulated through the circulation loop 1. As such, the amount x corresponds to an amount of the polymerization initiator aqueous solution which passes through the line mixer 6, and the amount y corresponds to an amount of the polymerization initiator aqueous solution which is fed to the next step.

The flow rate can be controlled by (i) measuring an amount of the polymerization initiator aqueous solution through each tube with a flowmeter, and (ii) operating a control valve so that the ratio of x/y falls within the above range.

The second tank 8 of the present invention is not particularly limited in terms of capacity. A suitable capacity is determined according to, e.g., a production amount of a water absorbing agent and a feeding amount of a polymerization initiator aqueous solution. In a case where, for example, the production amount of a particulate water absorbing agent is 23,000 kg/hr and the feeding amount of a polymerization initiator aqueous solution is 600 kg/hr, the second tank 8 will have a capacity which falls within a range from 0.8 to 1.2 $m^3$ and store a liquid amount of 500 L. The first tank 4 is also not particularly limited in terms of capacity. The capacity falls, for example, within a range from 2 to 4 $m^3$. As such, the apparatus 2 can save space.

In the present invention, the polymerization initiator aqueous solution stored in the second tank 8 is desirably cooled so as to prevent degradation of the polymerization initiator. The cooling of the aqueous solution is not particularly limited in method. The aqueous solution stored in the second tank 8 can be cooled, e.g., with a cooling device, provided to the second tank 8, such as a jacket, a coil, a plate type heat exchanger, and a shell-and-tube type heat exchanger. Since the second tank 8 has a small capacity, the aqueous solution can be sufficiently cooled even with a cooling device having a small output. In other words, the apparatus 2 can also save energy. Alternatively, a stirrer can be provided in the second tank 8, instead of using the circulation loop, so that the mixture solution in the second tank is stirred. In this case, the cooling is preferably carried out with a jacket or a coil.

The polymerization initiator aqueous solution in the second tank 8 preferably has a temperature which falls within a range from 2 to 20° C., and more preferably within a range from 5 to 15° C. It is possible to eliminate the need to use a special refrigerant by setting the temperature of the aqueous solution within one of the above ranges. This provides an economic advantage.

In the present invention, a ratio of C1/C2 preferably falls within a range from 2 to 50, and particularly preferably within a range from 5 to 45, where C1 is a concentration of the polymerization initiator in the aqueous solution (mother liquor) stored in the first tank 4, and C2 is a concentration of the polymerization initiator in the aqueous solution stored in the second tank 8. It is possible to reduce the respective capacities of the first tank 4 and the second tank 8 by setting the ratio (dilution ratio) within one of the above ranges.

The apparatus 2 illustrated in FIG. 1 provides a significant advantage in the case where the polymerization initiator aqueous solution has a low concentration, i.e., where the polymerization initiator aqueous solution is used in a large amount. In other words, since the polymerization initiator aqueous solution can be mixed sufficiently with a monomer aqueous solution, a water absorbing agent to be obtained has stable properties even in a case where an induction period for the polymerization reaction is short. Note that the induction period stands for a period from (i) a point when the polymerization initiator aqueous solution is added to a monomer aqueous solution to (ii) a point when a polymerization starts. The present invention is suitably applicable in a case where the induction period is not longer than 5 minutes, and more particularly not longer than 1 minute.

[Surface Cross-Linking Agent Solution Preparing Step]

In the present invention, a surface cross-linking agent solution can be prepared with use of any of the respective apparatuses illustrated in FIGS. 1 through 3. The description below specifically refers to FIG. 2, illustrating an apparatus which is particularly suitably applicable to the preparation of the surface cross-linking agent solution of the present invention.

The apparatus 20 illustrated in FIG. 2 includes: a first tank 22, a second tank 24, a third tank 26, a line mixer 28, a fourth tank 30, a first tube 32, a second tube 34, a third tube 36, a fourth tube 38, a fifth tube 40, and a sixth tube 42 (for a circulation loop). The first tube 32 connects the first tank 22 with the line mixer 28. The second tube 34 connects the second tank 24 with the first tube 32. The third tube 36 connects the third tank 26 with the second tube 34. The fourth tube 38 connects the line mixer 28 with the fourth tank 30. The fifth tube 40 connects the fourth tank 30 with a next step. The sixth tube 42 branches off from midstream of the fifth tube 40 and is connected back to the fourth tank 30. As such, a part of the fifth tube 40 and the sixth tube 42 together form a circulation loop (hereinafter referred to simply as "circulation loop 2").

In the present invention, each of the first tank 22, the second tank 24, and the third tank 26 is a tank for storing a raw material for use in preparation of a mixture solution containing surface cross-linking agents. Specifically, the first tank 22 stores a surface cross-linking agent (hereinafter referred to as "first surface cross-linking agent"), the second tank 24 stores another surface cross-linking agent (hereinafter referred to as "second surface cross-linking agent"), and the third tank 26 stores water. As such, since each of the first tank 22 and the second tank 24 stores a stock solution of a surface cross-linking agent, it is possible to reduce an amount of the surface cross-linking agent to be stored in each tank and thus reduce a capacity of each tank. Note that the third tank 26 may be omitted so that the water is directly poured into the second tube 34.

The first surface cross-linking agent stored in the first tank 22 is continuously taken out and transferred via the first tube 32 to the line mixer 28. The second surface cross-linking agent stored in the second tank 24 is continuously taken out and transferred via the second tube 34 to the first tube 32. The water stored in the third tank 26 is continuously taken out and transferred via the third tube 36 to the second tube 34. The first surface cross-linking agent, the second surface cross-linking agent, and the water are mixed in the line mixer 28. A resulting surface cross-linking agent mixture solution passes through the line mixer 28 and is then continuously poured into the fourth tank 30 via the fourth tube 38 so that a predetermined amount of the mixture solution is stored in the fourth tank 30. The mixture solution stored in the fourth tank 30 is continuously taken out via the fifth tube 40 and is then continuously added to water absorbent resin particles made of an acrylic acid (salt) polymer.

There has been a problem that since the surface cross-linking agents and the water are not sufficiently mixed in the line mixer 28, the mixture solution through the fourth tube 38 has an unstable and nonuniform mixing ratio. As such, if the surface cross-linking agent mixture solution through the fourth tube 38 is directly added to the water absorbent resin particles, a particulate water absorbing agent to be obtained will also have an unstable quality. In view of this, according to the present invention, the surface cross-linking agent mixture solution through the fourth tube 38 is temporarily stored in the fourth tank 30. This arrangement allows the mixture solution in the fourth tank 30 to be circulated via the circulation loop 2 so that the three kinds of liquids are sufficiently mixed with one another.

This method stabilizes the mixing ratio of the surface cross-linking agent mixture solution stored in the fourth tank 30. The mixing ratio of the surface cross-linking agent mixture solution stored in the fourth tank 30 is not particularly limited to a specific one. In the case where, for example, two kinds of surface cross-linking agents are used in combination, it is preferable that (i) the first surface cross-linking agent is contained in an amount which falls within a range from 1 to 30 mass %, (ii) the second surface cross-linking agent is contained in an amount which falls within a range from 1 to 30 mass %, and (iii) the water is contained in an amount which falls within a range from 40 to 98 mass %. Even in a case where a single kind of surface cross-linking agent is used or a case where three or more kinds of surface cross-linking agents are used, a content of each surface cross-linking agent can be determined as appropriate so that the water is contained in an amount which falls within the range from 40 to 98 mass %. The mixing ratio of the mixture solution is likely stabilized by setting the mixing ratio of the mixture solution within the above range. Since the surface cross-linking agent mixture solution through the fifth tube 40 has a stable mixing ratio, it is possible to produce a high-quality particulate water absorbing agent. The above plurality of surface cross-linking agents can preferably be either (i) a combination of two or more kinds of covalent bonding surface cross-linking agents or (ii) a combination of a covalent bonding surface cross-linking agent and an ionic bonding surface cross-linking agent (e.g., aluminum salt). Even in the case where a plurality of surface cross-linking agents are used, a particulate water absorbing agent to be obtained has stable properties, and also its production equipment is compact.

In the case where the two kinds of surface cross-linking agents and the water are mixed in a batch so as to prepare a mixture solution suitable to be added to water absorbent resin particles, a large amount of the mixture solution is required. This undesirably requires a large tank.

In view of this, according to the apparatus 20 illustrated in FIG. 2, the surface cross-linking agent mixture solution is continuously poured into the fourth tank 30, while the mixture solution is continuously taken out from the fourth tank 30. This allows the apparatus to operate while a liquid surface in the fourth tank 30 is controlled at a substantially constant level.

Specifically, a ratio of x/y preferably falls within a range from 0.95 to 1.05, where x is an amount of the surface cross-linking agent mixture solution poured into the fourth tank 30, and y is an amount of the surface cross-linking agent mixture solution taken out from the fourth tank 30. It is preferable that (i) a flow rate is controlled for each of the amounts x and y so that the ratio falls within the range, and also (ii) an amount of the surface cross-linking agent mixture solution stored in the fourth tank 30 is controlled so that the amount falls within a range from 10 to 90% of the capacity of the fourth tank 30. This arrangement allows a reduction in (i) the capacity of the fourth tank 30 and (ii) a period during which the surface cross-linking agent mixture solution is retained in the fourth tank 30. Note that neither of the amounts x and y includes an amount of the surface cross-linking agent mixture solution which is circulated through the circulation loop 2. As such, the amount x corresponds to an amount of the surface cross-linking agent mixture solution which passes through the line mixer 28, and the amount y corresponds to an amount of the surface cross-linking agent mixture solution which is fed to the next step.

The fourth tank 30 of the present invention is not particularly limited in terms of capacity. A suitable capacity is determined according to, e.g., a production amount of a water absorbing agent and a feeding amount of a surface cross-linking agent mixture solution. In a case where, for example, the production amount of a water absorbing agent is 23,000 kg/hr and the feeding amount of a surface cross-linking agent mixture solution is 600 kg/hr, the fourth tank 30 will have a capacity which falls within a range from 0.8 to 1.2 $m^3$ and store a liquid amount of 500 L. Neither of the first tank 22, the second tank 24, and the third tank 26 is particularly limited in terms of capacity, either. The capacity of each of the three tanks falls, for example, within a range from 10 to 40 $m^3$. As such, the apparatus 2 can save space.

[Additive Solution Preparing Step]

In the present invention, an additive solution can be prepared with use of any of the respective apparatuses illustrated in FIGS. 1 through 3. The description below specifically refers to FIG. 3, illustrating an apparatus which is particularly suitably applicable to the preparation of the surface crosslinking agent solution of the present invention.

The apparatus 44 illustrated in FIG. 3 includes: a first tank 46, a second tank 48, a third tank 50, a line mixer 52, a fourth tank 54, a first tube 58, a second tube 60, a third tube 62, a fourth tube 64, a fifth tube 66, and a sixth tube 68 (for a circulation loop). The first tube 58 connects the first tank 46 with the line mixer 52. The second tube 60 connects the second tank 48 with the first tube 58. The third tube 62 connects the third tank 50 with the first tube 58. The fourth tube 64 connects the line mixer 52 with the fourth tank 54. The fifth tube 66 connects the fourth tank 54 with a next step. The sixth tube 68 branches off from midstream of the fifth tube 66 and is connected back to the fourth tank 54. As such, a part of the fifth tube 66 and the sixth tube 68 together form a circulation loop (hereinafter referred to simply as "circulation loop 3").

In the present invention, each of the first tank 46, the second tank 48, and the third tank 50 is a tank for storing a raw material for use in preparation of a mixture solution containing an additive. Specifically, the first tank 46 stores an additive aqueous solution (mother liquor), the second tank 48 stores a first auxiliary dispersing agent (hereinafter referred to as "first auxiliary dispersing agent"), and the third tank 50 stores a second auxiliary dispersing agent (hereinafter referred to as "second auxiliary dispersing agent"). As such, since each of the first tank 46, the second tank 48, and the third tank 50 stores an additive aqueous solution (mother liquor), a stock solution of an auxiliary dispersing agent, or an aqueous solution (mother liquor) thereof, it is possible to reduce an amount of the solution to be stored in each tank and thus reduce a capacity of each tank. Note that the additive serves to modify surfaces of water absorbent resin particles, and the auxiliary dispersing agents serve to increase dispersibility of the additive.

The additive aqueous solution (mother liquor) stored in the first tank 46 is continuously taken out and transferred via the first tube 58 to the line mixer 52. The first auxiliary dispersing agent stored in the second tank 48 is continuously taken out and transferred via the second tube 60 to the first tube 58. The second auxiliary dispersing agent stored in the third tank 50 is continuously taken out and transferred via the third tube 62 to the first tube 58. The additive aqueous solution (mother liquor), the first auxiliary dispersing agent, and the second auxiliary dispersing agent are mixed in the line mixer 52. A resulting additive mixture solution passes through the line mixer 52 and is then continuously poured into the fourth tank 54 via the fourth tube 64 so that a predetermined amount of the mixture solution is stored in the fourth tank 54. The mixture solution stored in the fourth tank 54 is continuously taken out via the fifth tube 66 and is then continuously added to water absorbent resin particles made of an acrylic acid (salt) polymer.

There has been a problem that since the additive and the auxiliary dispersing agents are not sufficiently mixed in the line mixer 52, the mixture solution through the fourth tube 64 has an unstable and nonuniform mixing ratio. As such, if the additive mixture solution through the fourth tube 64 is directly added to the water absorbent resin particles, a particulate water absorbing agent to be obtained will also have an unstable quality. In view of this, according to the present invention, the additive mixture solution through the fourth tube 64 is temporarily stored in the fourth tank 54. This arrangement allows the mixture solution in the fourth tank 54 to be circulated via the circulation loop 3 so that the three kinds of liquids are sufficiently mixed with one another.

This method stabilizes the mixing ratio of the additive mixture solution stored in the fourth tank 54. In the case where each of the three kinds of additive and auxiliary agents are added in a form of an aqueous solution, the additive mixture solution stored in the fourth tank 54 has a mixing ratio which is determined as appropriate according to a kind of each agent and a form thereof (a solution or a neat liquid). A preferable example of the mixing ratio is as follows:

Agent A: from 20 to 95 mass %
Agent B: from 1 to 40 mass %
Agent C: from 0.5 to 30 mass %

The mixing ratio of the mixture solution is likely stabilized by setting the mixing ratio of the mixture solution within the above range. Since the additive mixture solution through the fifth tube 66 has a stable mixing ratio, it is possible to produce a high-quality particulate water absorbing agent. Note that even in a case where a single kind of additive is used or a case where three or more kinds of additive and auxiliary agents are used, the mixing ratio can be determined as appropriate so that water is contained in an amount which falls within a range from 40 to 98 mass %.

In the case where the additive and the two kinds of auxiliary dispersing agents are mixed in a batch so as to prepare a mixture solution suitable to be added to water absorbent resin particles, a large amount of the mixture solution is required. This undesirably requires a large tank.

In view of this, according to the apparatus 44 illustrated in FIG. 3, the additive mixture solution is continuously poured into the fourth tank 54, while the mixture solution is continuously taken out from the fourth tank 54. This allows the apparatus to operate while a liquid surface in the fourth tank 54 is controlled at a substantially constant level.

Specifically, a ratio of x/y preferably falls within a range from 0.95 to 1.05, where x is an amount of the additive mixture solution poured into the fourth tank 54, and y is an amount of the additive mixture solution taken out from the fourth tank 54. It is preferable that (i) a flow rate is controlled for each of the amounts x and y so that the ratio falls within the range, and also (ii) an amount of the additive mixture solution stored in the fourth tank 54 is controlled so that the amount falls within a range from 10 to 90% of the capacity of the fourth tank 54. This arrangement allows a reduction in (i) the capacity of the fourth tank 54 and (ii) a period during which the additive mixture solution is retained in the fourth tank 54. Note that neither of the amounts x and y includes an amount of the additive mixture solution which is circulated through the circulation loop 3. As such, the amount x corresponds to an amount of the additive mixture solution which passes through the line mixer 52, and the amount y corresponds to an amount of the additive mixture solution which is fed to the next step.

The fourth tank 54 of the present invention is not particularly limited in terms of capacity. A suitable capacity is determined according to, e.g., a production amount of a particulate water absorbing agent and a feeding amount of an additive mixture solution. In a case where, for example, the production amount of a particulate water absorbing agent is 23,000 kg/hr and the feeding amount of an additive mixture solution is 200 kg/hr, the fourth tank 54 will have a capacity which falls within a range from 0.8 to 1.2 $m^3$ and store a liquid amount of 300 L. Neither of the first tank 46, the second tank 48, and the third tank 50 is particularly limited in terms of capacity, either. The capacity of each of the three tanks falls, for example, within a range from 10 to 40 m³. As such, the apparatus 2 can save space.

In the present invention, the additive mixture solution stored in the fourth tank 54 is desirably heated so as to prevent deposition of the additive. The heating of the mixture solution is not particularly limited in method. The mixture solution stored in the fourth tank 54 can be heated, e.g., with a heating device, provided to the fourth tank 54, such as a jacket and a coil, or a heating device, provided to the circulation loop 3, such as a plate type heat exchanger and a shell-and-tube type heat exchanger. Since the fourth tank 54 has a small capacity, the mixture solution can be sufficiently heated even with a heating device having a small output. In other words, the apparatus 44 can also save energy. Alternatively, a stirrer can be provided in the fourth tank 54, instead of using the circulation loop 3, so that the mixture solution in the fourth tank is stirred. In this case, the heating is preferably carried out with a jacket or a coil.

The additive mixture solution in the fourth tank 54 preferably has a temperature which falls within a range from 35 to 70° C., and more preferably within a range from 40 to 60° C. It is possible not only to prevent deposition of the additive but also to eliminate the need to use a special heating medium, by setting the temperature of the aqueous solution within one of the above ranges. This provides an economic advantage.

(Particulate Water Absorbing Agent)

The particulate water absorbing agent produced by the production method of the present invention may contain a residue of an unpolymerized monomer containing an acid group. In view of stench prevention and hygiene, the particulate water absorbing agent preferably contains such a residual monomer in an amount which falls within a range from 0 to 500 ppm, more preferably within a range from 0 to 300 ppm, and particularly preferably within a range from 0 to 100 ppm. Employing the present invention allows a stable production of a particulate water absorbing agent which contains a residual monomer in an amount which falls within one of the above ranges. The amount of a residual monomer is measured as follows: First, 1000 g of deionized water is prepared in a lidded plastic container. Next, 0.5 g of the particulate water absorbing agent is added to the deionized water, which is then stirred for 2 hours. After the stirring, the water absorbing agent in a form of a swelling gel is filtered out with filter paper so that a resulting filtrate is analyzed by liquid chromatography. The same analysis is carried out with respect to a solution containing a monomer (acrylic acid) in a known concentration so that a working curve obtained is used as an external standard. The amount of a residual monomer is determined, on the basis of the external standard, by taking into consideration a dilution rate of the filtrate.

The present invention is applicable to various particulate water absorbing agents. The present invention is suitably applicable particularly as a method for producing a particulate water absorbing agent having high properties (high AAP and high SFC). The present invention achieves a particularly significant advantage in a case where, for example, the particulate water absorbing agent contains a polyacrylic acid (salt) water absorbent resin as a main component, and a case where (i) an absorbency against pressure (AAP) of the particulate water absorbing agent for physiological saline under 4.8 kPa falls within a range from 15 to 35 g/g, and/or (ii) a liquid permeability (SFC) of the particulate water absorbing agent is not less than 30 $(\times 10^{-7} \cdot cm^3 \cdot s \cdot g^{-1})$. This particulate water absorbing agent preferably contains a surface-cross-linked polyacrylic acid (salt) water absorbent resin, and more preferably, the surface cross-linking is carried out with the above surface cross-linking agent.

According to the particulate water absorbing agent of the present invention, a centrifuge retention capacity (referred to also as "CRC" in the present specification) for physiological saline preferably falls within a range from 15 to 60 g/g, and more preferably within a range from 25 to 50 g/g. It is possible to inexpensively produce a particulate water absorbing agent which has a good absorbing performance with respect to, e.g., a body fluid, by setting the CRC within one of the above ranges. Further, by employing the present invention, it is possible to stably produce such a particulate water absorbing agent having a centrifuge retention capacity (CRC) which falls within one of the above ranges.

According to the particulate water absorbing agent of the present invention, the absorbency against pressure (AAP) for physiological saline under 4.8 kPa preferably falls within a range from 15 to 35 g/g, more preferably within a range from 22 to 35 g/g, even more preferably within a range from 24 to 35 g/g, and particularly preferably within a range from 26 to 35 g/g. It is possible to inexpensively produce a particulate water absorbing agent which has a good absorbing performance with respect to, e.g., a body fluid, by setting the AAP within one of the above ranges. Further, by employing the present invention, it is possible to stably produce such a particulate water absorbing agent having an absorbency against pressure (AAP) which falls within one of the above ranges. In addition, a particulate water absorbing agent to be obtained in accordance with present invention has a small variation in property. Specifically, the present invention allows a standard deviation σ for the AAP to be controlled within a range from 0 to 0.25, within a range from 0 to 0.20, or particularly within a range from 0 to 0.15.

According to the particulate water absorbing agent of the present invention, the liquid permeability (SFC) is preferably not less than 30 $(\times 10^{-7} \cdot cm^3 \cdot s \cdot g^{-1})$, more preferably not less than 60 $(\times 10^{-7} \cdot cm^3 \cdot s \cdot g^{-1})$, and more preferably not less than 100 $(\times 10^{-7} \cdot cm^3 \cdot s \cdot g^{-1})$. It is possible to produce a particulate water absorbing agent which has a good absorbing performance with respect to, e.g., a body fluid, by setting the SFC within one of the above ranges. Note that the liquid permeability (SFC) is a value indicating a liquid permeability of a swollen water absorbing agent. By employing the present invention, it is possible to stably produce a particulate water absorbing agent having a liquid permeability (SFC) which falls within one of the above ranges. In addition, a particulate water absorbing agent to be obtained in accordance with present invention has a small variation in property. Specifically, the present invention allows a standard deviation σ for the SFC to be controlled within a range from 0 to 7, or particularly within a range from 0 to 5.

The above mixing is a method in which two or more kinds of liquids are continuously fed into a tank while a mixture solution of the liquids is continuously taken out from the tank. This method is applicable to various steps of the production of a water absorbing agent. A water absorbing agent, which is produced in a large-scale plant, needs to be produced stably in the large-scale plant. This production is carried out in accordance with a method which requires strict control of respective use amounts of, e.g., a polymerization initiator, a surface cross-linking agent, and an additive. The above mixing method achieves a particular advantage when used in such a production method. Further, the mixing method achieves a particular advantage when used in a method of continuous production in which a production amount of a particulate water absorbing agent per one line (one plant) is not less than 1000 kg/hr, not less than 2000 kg/hr, and particularly not less than 4000 kg/hr. A particulate water absorbing agent can be mass-produced by continuously carrying out the respective steps of, e.g., polymerization, drying, classification, and surface cross-linking. The present invention can solve problems (decrease and variation in property) peculiar to such a mass production.

Note that the present invention regards a production as continuous whose entire flow, including a storing step and the like, is continuous, even if the production includes a batch step (e.g., batch polymerization) partially. The respective steps of polymerization, drying, classification, and surface cross-linking are preferably connected to one another for a continuous production.

EXAMPLES

The following description deals with advantages of the present invention with reference to an Example. The present invention should, however, not be limitedly interpreted on the basis of the description of the Example.

(Measurement of CRC)

The centrifuge retention capacity (CRC) for physiological saline is measured as follows: First, 0.2 g of a particulate water absorbing agent (this mass corresponds to a mass W1 (g) of the particulate water absorbing agent) is accurately measured out, and is uniformly contained in a nonwoven fabric bag (60 mm×85 mm). Next, the bag is soaked in a physiological saline whose temperature has been adjusted to 25±2° C., and the bag is then kept therein for 30 minutes. After the 30 minutes, the bag is taken out from the saline and is drained for 3 minutes in a centrifuge (H-122; compact centrifuge manufactured by KOKUSAN Corporation) at 250 G (250×9.81 m/s$^2$). Then, a mass W2 (g) of the bag is measured. The same measurement is made of a bag containing no particulate water absorbing agent to obtain a mass W3 (g) of the bag. The centrifuge retention capacity (CRC) is finally found from the following equation.

$$CRC\ (g/g)=((W2-W3)/W1)-1$$

(Measurement of AAP)

The absorbency against pressure (AAP) is measured as follows: First prepared is a plastic supporting cylinder having an internal diameter of 60 mm. To a bottom of the supporting cylinder, a stainless steel net is fusion-bonded. This net is of 400 mesh (mesh size: 38 μm). Further prepared is a piston (cover plate) which is slidable in an up-and-down direction and which has an external diameter which is smaller than 60 mm only slightly so that there is no gap between the piston and a wall surface of the supporting cylinder. On the net, 0.900 g of the particulate water absorbing agent is uniformly spread out. (During this step, a mass W4 of the particulate water absorbing agent is measured.) Next, the piston is placed on the particulate water absorbing agent, and a total mass W5 (g) of the supporting cylinder, the particulate water absorbing agent, and the piston is measured. A weight is placed on the piston so that a pressure of 4.8 kPa is uniformly applied to the particulate water absorbing agent. Then, a glass filter having a diameter of 90 mm and a thickness of 5 mm is placed in a petri dish having a diameter of 150 mm. A physiological saline whose temperature has been adjusted to 25±2° C. is poured into the petri dish so that a level of the saline corresponds to an upper surface of the glass filter. On the upper surface of the glass filter, a piece of filter paper (No. 2; manufactured by Toyo Roshi Kaisha, Ltd.) having a diameter of 9 cm is placed so that an excess saline is removed. The supporting cylinder and the piston are placed above the petri dish so that the net is in contact with the filter paper. In a case where the level of the saline becomes lower than the upper surface of the glass filter, more saline is added so that the surface of the saline is kept at a constant level. After 1 hour, the supporting cylinder and the piston are removed from the petri dish so that a mass W6 (g), exclusive of a mass of the weight, is measured. The mass W6 (g) includes a mass of the water absorbing agent which is swollen due to the physiological saline. The absorbency against pressure (AAP) is finally found from the following equation.

$$AAP\ (g/g)=(W6-W5)/W4$$

The measurement is made at a temperature of 23±2° C. This measuring method is disclosed in U.S. Pat. No. 6,071,976.

(Measurement of SFC)

The liquid permeability (SFC) is measured as follows: First, 0.900 g of a particulate water absorbing agent is uniformly contained in a container. The particulate water absorbing agent is soaked in synthesized urine and is kept under a pressure of 2.07 kPa. After 60 minutes, a height of a resulting swollen water absorbing agent (gel layer) is measured. While the particulate water absorbing agent is under the pressure of 2.07 kPa, 0.69 mass % saline is caused to pass through the gel layer. During this step, a room temperature is adjusted to a temperature which falls within a range from 20° C. to 25° C. An amount of the liquid through the gel layer is recorded at 20-second intervals with a computer and a balance so that a flow rate Fs (T) of the liquid through the gel layer is found. The flow rate Fs (T) is found by dividing a mass increase (g) by a duration (s) for the increase. The flow rate is found on the basis of only data obtained by a measurement made during a 10-minute period after Ts, which is a point in time at which point a hydrostatic pressure of the saline becomes constant and a stable flow rate is thus obtained. A value of Fs (T=0) is obtained from the flow rate found by a 10-minute measurement made after Ts. This value indicates a first flow rate of the liquid through the gel layer. Fs (T=0) is found by plotting Fs (T) against the duration and obtaining a result of carrying out least square of Fs (T) and the duration. The liquid permeability (SFC) is finally found from the following equation.

$$SFC=(Fs(t=0) \cdot L0)/(\rho \cdot A \cdot \Delta P),$$

where L0 is the height (cm) of the gel layer, ρ is a density (g/cm$^3$) of the saline, A is a sectional area A (cm$^2$) of the gel layer, and ΔP is a hydrostatic pressure (dyne/cm$^2$) on the gel layer. The above synthesized urine is an aqueous solution having the following composition: calcium chloride dihydrate: 0.025 mass %, potassium chloride: 0.2 mass %, magnesium chloride hexahydrate: 0.05 mass %, sodium sulfate: 2 mass %, ammonium dihydrogen phosphate: 0.085 mass %, and diammonium hydrogen phosphate: 0.015 mass %. The evaluation of the SFC is carried out in accordance with an SFC test described in the specification of U.S. Pat. No. 5,849,405.

Example 1

A particulate water absorbing agent was continuously produced at approximately 1800 kg/hr with production equipment which included respective apparatuses for the polymerizing step (including pulverization), the drying step, the pulverizing step, the classifying step, the surface cross-linking step (including a step for spraying a surface cross-linking agent and a step for heating it), the cooling step, the additive adding step, the granulating step, and the storing/filling step. The apparatuses were connected to one another so that the above steps were carried out continuously. The following description deals in detail with a method of the production.

First prepared was a reactor constituted by a lidded double-arm kneader (made of stainless steel) having two sigma blades and an attached jacket. In this reactor, a monomer aqueous solution having a concentration of 37 mass % was poured. The monomer aqueous solution contained an acrylic acid and acrylic acid sodium salt as a monomer. The monomer aqueous solution had a neutralization ratio of 73 mol %. The monomer aqueous solution contained 0.06 mol % (with respect to the monomer) polyethyleneglycol diacrylate (average number n: 9) serving as an internal cross-linking agent. The monomer aqueous solution was deaerated under nitrogen gas atmosphere. Additionally prepared were a sodium persulfate aqueous solution and an L-ascorbic acid aqueous solution each serving as a polymerization initiator. The sodium persulfate aqueous solution was prepared as follows: To add 0.12 g of sodium persulfate to 1 mol of the monomer in the apparatus 2 illustrated in FIG. 1, (i) a 30 mass % sodium persulfate aqueous solution was prepared in the first tank 4, (ii) water was then continuously added to the aqueous solution, and (iii) a resulting mixture was mixed in the line mixer 6, so that a 2 mass % sodium persulfate aqueous solution was obtained in the second tank 8. Further, to add 0.005 g of L-ascorbic acid to 1 mol of the monomer, a 0.5 mass % aqueous solution was prepared in a manner similar to the above. These aqueous solutions were separately added to the monomer aqueous solution to start a polymerization reaction, which in turn provided a gel. The polymerization reaction was promoted while the gel was pulverized. A hydrogel was taken out from the reactor 30 minutes after the start of the polymerization.

The polymerization had a stable induction period and peak temperature period of approximately 30 seconds and 10 minutes, respectively. The apparatus can be compact and the polymerization can be stable in the case where a polymerization initiator aqueous solution having a desired concentration is prepared through two stages.

Next, the hydrogel was placed on a porous plate of a continuous circulation band dryer. The dryer was operated at 185° C. for 30 minutes so that the hydrogel was dried. This provided a dried polymer. This dried polymer was continuously fed into a three-stage roll mill so that the dried polymer was pulverized. This provided water absorbent resin particles (1). These particles were put into a classification device for classification which device included metal screens having respective mesh sizes of 850 μm and 150 μm. Among particles separated by this classification, a ratio of particles each having a particle size ranging from 150 μm to 850 μm was 98 mass %. The water absorbent resin particles (1) were continuously fed into a high-speed continuous mixer (Turbulizer; rotation speed: 1000 rpm). An amount of the feeding was 1800 kg/hr. In this mixer, a surface cross-linking agent aqueous solution was sprayed onto surfaces of the water absorbent resin particles (1). The aqueous solution contained: 0.3 part by mass of 1,4-butandiol; 0.5 part by mass of propylene glycol; and 2.7 parts by mass of pure water, with respect to 100 parts by mass of the water absorbent resin. This solution was continuously fed into the mixer after it was continuously prepared in the apparatus 20 illustrated in FIG. 2. In this apparatus, 1,4-butandiol, propylene glycol, and pure water were continuously fed into the fourth tank (capacity: 1000 L). Specifically, the 1,4-butandiol was fed from the first tank to the fourth tank in an amount of 4 kg/hr, the propylene glycol was fed from the second tank to the fourth tank in an amount of 9.0 kg/hr, and the pure water was fed from the third tank to the fourth tank in an amount of 48.6 kg/hr.

The above water absorbent resin particles were continuously fed into a paddle dryer so as to be heated at 198° C. for 40 minutes. The water absorbent resin particles were then forcedly cooled down to 60° C. in the same paddle dryer. During the cooling, an additive solution was added to the particles in a temperature zone of approximately 90° C. This solution contained: 0.5 part by mass of aluminum sulfate hydrate (tetradecahydrate to octadecahydrate); 0.2 part by mass of sodium lactate; and 0.03 part by mass of propylene glycol, with respect to 100 parts by mass of the water absorbent resin.

The particles were taken out from the paddle dryer, and were then put into a classification device for classification which device included a metal screen having a mesh size of 850 μm. Particles which had not passed through the screen were pulverized and were then mixed with particles which had passed through the screen. This treatment provided a particulate water absorbing agent whose particles would all pass through the screen having a mesh size of 850 μm. This particulate water absorbing agent was packed fully in a packaging container.

Comparative Example 1

A particulate water absorbing agent was obtained in the same manner as in Example 1, except that a surface cross-linking agent aqueous solution was prepared in batch. According to this method, 190 L of propylene glycol, 140 L of 1,4-butandiol, and 1110 L of pure water were put into a large tank having a capacity of 2000 L. A resulting mixture was stirred in this large tank so that a surface cross-linking agent solution was obtained. This solution was transferred as appropriate from the large tank to a relay tank having a capacity of 600 L. The solution was continuously fed from the relay tank to the paddle dryer.

[Measurement of Property Values]

The absorbency against pressure (AAP) and liquid permeability (SFC) of each water absorbing agent obtained were measured. Sampling and measurement were carried out ten times to find a standard deviation σ for each property. Table 1 shows a result of evaluation.

TABLE 1

| | | Evaluation Result | |
|---|---|---|---|
| | | Example 1 | Comparative Example 1 |
| Tank used for mixing | | Fourth tank (Capacity: 1000 L) | Large tank (Capacity: 2000 L) Relay tank (Capacity: 600 L) |
| Standard deviation | AAP | 0.22 | 0.32 |
| | SFC | 4.15 | 8.20 |

As shown in Table 1, equipment (one tank; total capacity: 1000 L) required in the production method of Example 1 is compact and easy to maintain, as compared to equipment (two tanks: total capacity: 2600 L) required in the production method of Comparative Example 1. Moreover, the particulate water absorbing agent obtained by the production method of Example 1 is excellent in property stability (standard deviations σ for the AAP and SFC) as compared to the particulate water absorbing agent obtained by the production method of Comparative Example 1. This is despite the fact that Comparative Example 1 uses the surface cross-linking agent (including butandiol, propylene glycol, and aluminum sulfate (added later)) in an amount equal to that of the surface cross-linking agent used in Example 1. The evaluation result thus clearly indicates superiority of the present invention.

The method of the present invention for producing a particulate water absorbing agent allows a uniform mixing of a liquid containing a polymerization initiator and/or a liquid containing a modifier for preparation thereof, and thus allows a mixture solution having no concentration variation to be obtained continuously. This in turn allows the polymerization initiator and/or modifier to be uniformly mixed with the water absorbent resin, and thus allows a stable and continuous production of a high-quality water absorbing agent. The method of the present invention further allows a reduction in capacity of a tank for use in preparation of the mixture solution, and thus allows downsizing of a plant, thereby saving space. In addition, the method of the present invention allows a reduction in, e.g., retention amount and storage amount of the liquid containing the polymerization initiator and/or the liquid containing the modifier, and thus allows a reduction in temporal decomposition and degradation of the liquid containing the polymerization initiator and/or the liquid containing the modifier. The method of the present invention consequently makes it possible to stabilize properties of a particulate water absorbing agent to be obtained, and thus achieves the greatest advantage particularly for a huge-scale continuous production. Furthermore, the method of the present invention allows a reduction in amount of the liquid containing the polymerization initiator and/or the liquid containing the modifier which remains when a production plant is stopped and which is thus to be discarded. The method of the present invention is thus environmentally friendly as well.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided that such variations do not exceed the scope of the patent claims set forth below.

INDUSTRIAL APPLICABILITY

The production method of the present invention allows a production of a water absorbing agent which is suitably applicable to sanitary materials such as a disposable diaper, a sanitary napkin, and an incontinence pad. The water absorbing agent can further be used as, e.g., an agricultural material and a civil engineering material.

The invention claimed is:

1. A method for producing a particulate water absorbing agent containing, as a main component, a water absorbent resin whose surface is cross-linked, the method comprising the steps of:
(1) mixing, with an aqueous solution of a monomer for a water absorbent resin, an aqueous solution containing a polymerization initiator;
(2) polymerizing the monomer so as to obtain a hydrogel;
(3) drying the hydrogel so as to obtain a dried polymer;
(4) cross-linking a surface of the water absorbent resin;
(5) adding, to the hydrogel or the dried polymer, a liquid containing a modifier, and
(6) producing the liquid containing the modifier by a method comprising the steps of:
(a) providing at least one kind of liquids in at least one tank;
(b) removing the at least one kinds of liquid from the at least one tank and mixing the at least one kind of liquid with a liquid separately prepared by a mixing device provided in a tube connecting the at least one tank to a storage tank to produce a mixture solution thus obtained;
(c) continuously taking out a part of the resulting mixture solution from the storage tank while continuously feeding the resulting mixture solution to the storage tank,
the modifier being a surface cross-linking agent which is used in the step (4),
in the step (a), the at least one kind of liquid provided in the at least one tank being a stock solution of the surface cross-linking agent, and
in the step(b), the liquid separately prepared being water and the step of said mixing being performed with use of the water to dilute the stock solution of the surface cross-linking agent removed from the at least one tank wherein the water absorbing agent is continuously produced at not less than 1000 kg/hr per one line or per one plant.

2. The method according to claim 1, wherein, step (c) further comprises circulating the part of the mixture solution in the storage tank via a circulation loop back to the storage tank.

3. The method according to claim 2, further comprising cooling or heating the part of the mixture solution in the circulation loop.

4. The method according to claim 1, further comprising cooling or heating the mixture solution in the storage tank.

5. The method according to claim 1, wherein the at least one kind of surface cross-linking agent is contained in an amount of not less than 0.001 part by mass but not more than 10 parts by mass with respect to 100 parts by mass of a solid content of the polymer.

6. The method according to claim 1, wherein, the step (a) the further comprises adding a surface cross-linking agent and an additive for use after surface cross-linking to the at least one tank to produce said at least one kind of liquid.

7. The method according to claim 1, wherein:
in the step (b) and step (c), a flow rate is controlled to satisfy $0.95 \leq x/y \leq 1.05$, where x is an amount of the at least one kind of mixture solution fed to the storage tank and y is an amount of the at least one kind of mixture solution taken out from the storage tank; and
the at least one kind of liquid is stored in the storage tank in an amount which is controlled so that the amount is not less than 10% but not more than 90% of a capacity of the storage tank.

8. The method according to claim 1, wherein:
the water absorbent resin comprises a polyacrylic acid water absorbent resin and/or a polyacrylic acid salt water absorbent resin; and
the polymerization is a continuous kneader polymerization or a continuous belt polymerization.

9. The method according to claim 1, wherein at least one dehydration esterification surface cross-linking agent selected from the group consisting of an oxazolidinone compound, an alkylenecarbonate compound, a polyhydric alcohol compound, and an oxetane compound is added to the dried polymer as the modifier.

10. The method according to claim 1, wherein a plurality of covalent bonding or ionic bonding surface cross-linking agents are added as the modifier to the dried polymer either simultaneously or separately.

11. The method according to claim 1, wherein the polymerization initiator is a water-soluble pyrolytic polymerization initiator which is used in combination with a reducing agent.

12. The method according to claim 1, wherein:
- the particulate water absorbing agent contains a polyacrylic acid-based water absorbent resin and/or a polyacrylic acid salt-based water absorbent resin as the main component; and
- (i) an absorbency against pressure of the particulate water absorbing agent for physiological saline under a pressure of 4.8 kPa falls within a range from 15 g/g to 35 g/g, and/or (ii) a liquid permeability of the particulate water absorbing agent is not less than $30(\times 10^{-7} \cdot cm^3 \cdot s \cdot g^{-1})$.

13. The method of claim 1, wherein said step (b) further comprises
- passing said at least one kind of liquid thus removed from the tank through an in-line mixer between said at least one tank in which the liquid has been provided and said storage tank.

14. The method according to claim 1, wherein the polymerization initiator is a water-soluble pyrolytic polymerization initiator which is used in combination with a reducing agent.

* * * * *